(12) United States Patent
Wurst

(10) Patent No.: US 10,204,704 B1
(45) Date of Patent: Feb. 12, 2019

(54) SYSTEMS AND METHODS FOR BIOMETRICALLY RETRIEVING MEDICAL INFORMATION

(71) Applicant: Brooke Erin Wurst, Boston, MA (US)

(72) Inventor: Brooke Erin Wurst, Boston, MA (US)

( * ) Notice: Subject to any disclaimer, the term of this patent is extended or adjusted under 35 U.S.C. 154(b) by 682 days.

(21) Appl. No.: 14/720,454

(22) Filed: May 22, 2015

Related U.S. Application Data

(63) Continuation-in-part of application No. 12/698,000, filed on Feb. 1, 2010, now Pat. No. 9,501,618.

(60) Provisional application No. 62/001,805, filed on May 22, 2014, provisional application No. 61/149,511, filed on Feb. 3, 2009.

(51) Int. Cl.
G06F 7/04 (2006.01)
G06F 19/00 (2018.01)
G16H 10/60 (2018.01)

(52) U.S. Cl.
CPC ............ *G16H 10/60* (2018.01); *G06F 19/00* (2013.01)

(58) Field of Classification Search
CPC .... G06F 19/322; G06F 19/00; G06F 19/3418; G06F 19/326; G06F 21/32; G06F 19/3456; G06Q 50/24
See application file for complete search history.

(56) References Cited

U.S. PATENT DOCUMENTS

| | | | |
|---|---|---|---|
| 5,823,948 A | 10/1998 | Ross, Jr. et al. | |
| 6,185,316 B1 | 2/2001 | Buffam | |
| 6,202,151 B1 * | 3/2001 | Musgrave | G06Q 20/04 713/170 |
| 6,408,330 B1 | 6/2002 | DeLaHuerga | |
| 7,415,138 B2 | 8/2008 | Schneider et al. | |
| 2002/0081005 A1 | 6/2002 | Black | |
| 2002/0188452 A1 * | 12/2002 | Howes | G06F 17/243 704/270 |
| 2003/0093298 A1 | 5/2003 | Hernandez et al. | |
| 2003/0131247 A1 * | 7/2003 | Cannon | G06F 21/10 713/186 |
| 2004/0025046 A1 * | 2/2004 | Blume | G06F 21/31 726/5 |
| 2004/0078217 A1 | 4/2004 | Bacevice et al. | |
| 2004/0177097 A1 | 9/2004 | Yu et al. | |
| 2004/0193448 A1 | 9/2004 | Woodbridge et al. | |
| 2005/0125258 A1 | 6/2005 | Yellin et al. | |
| 2005/0154920 A1 | 7/2005 | Tartaglia et al. | |

(Continued)

OTHER PUBLICATIONS

Zvetco Biometrics LLC, Biometric Fingerprint Software, "A Leader in Biometric Fingerprint Security Solutions", http://www.zvetcobiometrics.com/, [2010], 2 pages.

*Primary Examiner* — Maroun P Kanaan
(74) *Attorney, Agent, or Firm* — K&L Gates LLP

(57) ABSTRACT

In part, the disclosure relates to an apparatus, system, and method for responding to emergency needs of a user with one or more responses including contacting an emergency contact for a user in response to a biometric identifier. Other responses can include retrieving stored medical information for use by a first responder, insurance provider, medical or healthcare professional, or other user or entity. Emergency data retrieval software can be activated on a per user based upon a biometric scan of the user to trigger one or more data transmission or retrieval events such as medical file retrieval and emergency contacts being automatically called or messaged.

20 Claims, 26 Drawing Sheets

(56) References Cited

U.S. PATENT DOCUMENTS

| | | |
|---|---|---|
| 2005/0160052 A1 | 7/2005 | Schneider et al. |
| 2005/0229007 A1 | 10/2005 | Bolle et al. |
| 2005/0246541 A1 | 11/2005 | Ginter et al. |
| 2005/0278197 A1 | 12/2005 | Podczerwinski et al. |
| 2005/0281439 A1 | 12/2005 | Lange |
| 2006/0136744 A1 | 6/2006 | Lange |
| 2006/0293925 A1 | 12/2006 | Flom |
| 2007/0043594 A1 | 2/2007 | Lavergne |
| 2007/0047770 A1 | 3/2007 | Swope et al. |
| 2007/0214002 A1* | 9/2007 | Smith ................ G06F 19/328 705/2 |
| 2007/0258626 A1 | 11/2007 | Reiner |
| 2007/0279187 A1 | 12/2007 | Hekmatpour et al. |
| 2008/0072064 A1 | 3/2008 | Franchi |
| 2008/0177569 A1 | 7/2008 | Chen et al. |
| 2008/0181465 A1 | 7/2008 | Sauerwein |
| 2008/0191839 A1 | 8/2008 | Sato |
| 2008/0211627 A1 | 9/2008 | Shinzaki |
| 2008/0215890 A1 | 9/2008 | Buer |
| 2008/0300719 A1* | 12/2008 | Duke .................... A61J 7/0481 700/244 |
| 2009/0006439 A1 | 1/2009 | Joseph et al. |
| 2009/0009284 A1 | 1/2009 | Sako |
| 2009/0019552 A1* | 1/2009 | McLaughlin ......... G06F 19/322 726/27 |
| 2009/0021349 A1 | 1/2009 | Errico et al. |
| 2009/0141948 A1 | 6/2009 | Nakaoka et al. |
| 2009/0197563 A1* | 8/2009 | Yasrebi ............. H04M 3/42357 455/404.1 |
| 2009/0261947 A1 | 10/2009 | Watanabe et al. |
| 2009/0289761 A1 | 11/2009 | Janke et al. |
| 2009/0309700 A1 | 12/2009 | Fujita |
| 2009/0322477 A1 | 12/2009 | Celorio |
| 2010/0045431 A1 | 2/2010 | Nagamura et al. |
| 2010/0067747 A1 | 3/2010 | Perruchot et al. |
| 2010/0079242 A1 | 4/2010 | Martis et al. |

* cited by examiner

User interface after password verified

PRE-TEST COUNSELLING & QUESTIONNAIRE 148

GENERAL

How did you hear about this testing session? Community Center

Why have you come for a test today?
To test the application

Before today, how many times have you been tested for HIV?
None

HIV SOCIAL RISK FACTORS

1. How old were you when you first had sex?
2. (a) Have you ever felt forced into having sex? ☐ Yes ☑ No
   (b) Have you ever forced someone else to have sex? ☐ Yes ☑ No
3. Have you ever had sex for money, food, or clothing? ☐ Yes ☑ No
4. How many different sex partners have you had?
5. Type of partner? ☐ male ☐ female ☐ both
6. Do you know where you can get condoms? ☐ Yes ☑ No
7. Have you ever used condoms? ☐ Yes ☑ No
8. Do you know how to use condoms? ☐ Yes ☑ No
9. Have you ever used drugs or drank excessive alcohol? ☐ Yes ☑ No

HEALTH AWARENESS

10. To whom do you go for help when you are sick? doctor
11. How many times have you had diarrhea this year?
12. Was it ever bloody? ☐ Yes ☑ No
13. How many times have you had high fevers?
14. How many times have you seen a medical doctor at a clinic or hospital?
15. Have you ever had malaria? ☐ Yes ☑ No
16. Have you ever used medications for tuberculosis? ☐ Yes ☑ No
17. Do you use soap every day? ☐ Yes ☑ No
18. How do you think your life would change if you were diagnosed with HIV?

Informed Consent ☐

VCT Counsellor Assigned

[Return]

MEDICAL HISTORY / POST TEST QUESTIONNAIRE  ID: 148

1. Are you pregnant? ☐ Yes ☑ No
2. Are you breastfeeding? ☐ Yes ☑ No
3. Have you been to the hospital in last 6 months? ☐ Yes ☑ No
4. Are you currently receiving TB treatment? ☐ Yes ☑ No
5. Do you have diarrhea? ☐ Yes ☑ No
6. Do you have urinary pain? ☐ Yes ☑ No
7. Do you have parasites? ☐ Yes ☑ No
8. Do you have fevers? ☐ Yes ☑ No
9. Have you experienced any weight loss? ☐ Yes ☑ No
10. Do you have night sweats? ☐ Yes ☑ No
11. Do you have chills? ☐ Yes ☑ No
12. Do you take drugs? ☐ Yes ☑ No
13. Do you drink alcohol? ☑ Yes ☐ No
14. Do you use tobacco? ☐ Yes ☑ No VCT Counsellor Assigned _____

[Submit]

FIG. 4D

Patient Found: NAME

Basic Information

| FIRST NAME | LAST NAME |
| NAME | |

CODE STATUS
N/A

ADDRESS
San Francisco, CA 94602

| BLOOD TYPE | HEIGHT | WEIGHT | GENDER |
| AB+ | | | Male |

| BIRTHDAY | LANGUAGES |
| | English |

Insurance Information

EMERGENCY CONTACTS
Edward .
(415) 555-1972

Betsy
(650) 555-4602

COMPANY
Blue Shield of CA

| INSURANCE ID NUMBER | PLAN NAME |
| | Gold PPO |

Medical Information

ALLERGIES
Mold, Penicillin, Shellfish, Tree Nuts

FIG. 12F

SYSTEMS AND METHODS FOR BIOMETRICALLY RETRIEVING MEDICAL INFORMATION

CROSS-REFERENCE TO RELATED APPLICATIONS

This application claims priority to and the benefit of U.S. Provisional Application No. 62/001,805 filed May 22, 2014, and is a continuation in part of U.S. Non-provisional application Ser. No. 12/698,000 filed Feb. 1, 2010, which claims priority to and the benefit of U.S. Provisional Application No. 61/149,511 filed Feb. 3, 2009, the entire disclosures of each of which are hereby incorporated by reference herein for all purposes.

BACKGROUND

Written records and electronic records are important organizational tools for researchers and practitioners in many fields, such as health care, education, social services, and business management. Traditional written records and electronic records (databases) are only as secure as the media in which they are written. Two significant concerns for many hoping to use database records in remote areas of the world are confidentiality and connectivity.

Using local sources—such as written records or local computer hard drives—for recording sensitive database contents, is not desirable. If the written record is stolen, or the local computer crashes, the security of the data is compromised. Written databases with sensitive data are easy targets for thieves or those hoping to compromise the integrity of the data. The security of and access to electronic databases are subject to several factors—computer hard drive reliability, access to electricity, and the physical integrity of the computer itself, just to name a few.

There are also various challenges relating to the exchange of medical information in the case of emergencies and the admissions or intake process for medical facilities. Individuals in emergencies often have no way to communicate life-saving information to first responders and emergency medical personnel—current medications, relevant history, allergies. This lack of information leads to loss of life, treatment errors, and billions of dollars in avoidable costs to providers, hospital systems, and insurers.

Existing, niche-based services for emergency health alert systems have various limitations. Many of these services typically require wearing jewelry or a transponder, which require proximity to a receiver. Other technology such as QR codes do nothing to protect subscribers' identity or to secure the data shared at the time of service provision from anyone with a QR reader from accessing a user's sensitive information. They require first responders to look somewhere—a wallet, a shoe, a purse—for a QR code, which may or may not exist.

Therefore, a need exists for devices, methods and systems that address the underlying problems relating to collecting data from remote locations and populations which desire to remain anonymous or have secure but restricted access to their medical information. A need also exists for systems, methods and devices to address the problems identified above with regard to emergency services and first responder related data delivery.

SUMMARY

The present disclosure is related generally to data retrieval and user authentication techniques. More particularly, the present disclosure is related to medical data retrieval using a biometric identifier. In part, the disclosure relates to a mobile biometric emergency system and related services, methods, devices, and networks for end users that also provide a life-saving tool for service providers—all with just the swipe of a finger. Other biometric identifiers can be used in addition to a fingerprint scan, such as retinal scans, voice recognition, and facial recognition in various embodiments. The disclosure thus generally relates, in one embodiment, to crisis and emergency record management systems, methods, devices and software that use biometric identifiers to transmit records and manage aspects of a given crisis such as an incident or a mass casualty incident. Emergency data retrieval software can be activated on a per user basis upon a biometric scan of the user to trigger one or more data transmission or retrieval events such as medical file retrieval and emergency contacts being automatically called or messaged.

Prior to discussing the aspects of the first responder data exchange and medical data related systems and methods in detail, an introduction to some of the characteristic terminology used herein may prove informative. However, the scope of the terms discussed herein is not intended to be limiting, but rather to clarify their usage and incorporate the broadest meaning of the terms as known to those of ordinary skill in the art. Specifically, some of the terms that are summarized herein include subscriber or user, first responder, Rx Database, ePCR, CAD, scanpoint, incident, and mass casualty/harm incident.

Subscriber includes a person enrolling in the system/"the patient" in an emergency care scenario. User includes an authorized care provider (first responder, EMT, firefighter, paramedic, doctor, nurse, and other specific provider categories). The terms user and subscriber can be used interchangeably and include the scope of both terms as recited herein. The term user refers also to an individual using a mobile device or computing device running one or more software applications described herein to facilitate treating users such as by a first responder. First responder includes healthcare, governmental, and other aid givers such as Emergency Medical Technician (EMT), firefighter, paramedic, police, non-hospital-based care providers, ambulance drivers, doctors and nurses. For example, doctors and nurses may be serving a community outside hospital and be considered a first responder.

Rx Database includes a central national database of electronically transmitted prescriptions (Rxs). Sure Scripts is an example of an Rx Database. Incident includes and event or a situation requiring emergency medical attention and care or medical attention. Mass Casualty/Harm Incident or MCI includes an incident in which a high number and/or a high severity of casualties or high number of individuals requiring attention and care. During a MCI, care providers are overwhelmed or may be facing significantly higher numbers of patients relative to what they can handle. A MCI can include a two-person crew responding to a 3-car accident or a massive scale incident like a plane crash where there are survivors or a terrorist attack with survivors.

ePCR or electronic patient care reporting software includes third-party electronic patient care reporting software systems used by first responders such as firefighters/EMT. The ePCR software can include incident information and patient information. Information from ePCR can be passed along to a hospital at the time of patient transport/transfer, including in draft or preliminary form. A full report is sent by the ePCR to one or more levels of administration when more information is available or based upon rules specifying format and content for the information. The system and related methods have the ability to synchronize data files and selectively transfer data via an API designed based upon the interfaces of the emergency data retrieval and communication software into third party EMS electronic Patient Care Record (ePCR) reporting systems.

CAD or computer-assisted dispatch includes a dispatch system used to communicate information at the first responder agency level. Information received by the 911 call is dispatched to responders via a CAD. Such a system sends out incident information such as location, impression (suspected "type" of medical emergency such as heart attack, broken leg, car accident with multiple injuries), name, if known, age, description of patient. These systems may be run at a local/town level or county level.

A ScanPoint or scanpoint refers to a location having a biometric scanner in connection with a mobile device or computer running the emergency data retrieval/communication software by which a user can be scanned to capture the user's fingerprints or other recognition feature and create an identifier suitable for subsequent record retrieval and communication triggers when scanned in the future.

When operating at the local level, these systems often send information to or from county servers. A "mobile device" includes, without limitation, mobile phones, remote control devices, personal digital assistants, hand-held computers, ultra-mobile personal computers, and the like. The term "automatically" means without human intervention. Data sources can include data entered by an individual or entity. Data sources can include subscriber-entered data or third party sources such as the electronic prescription aggregator or advanced care directive database or a provider-system's electronic health records.

The ability to provide user identification and data retrieval in an emergency scenario benefits everyone who might need emergency care. By lowering cost barriers and removing requirements such as alert bracelets, pendants, and transponders, the systems and methods and related embodiments offer more robust emergency support and life-saving information to first responders than existing services.

In part, the disclosure relates to software applications and systems that give first responders access to an individual's essential medical information in an emergency using nothing more than that person's fingerprint or other biometric identifier. The mobile protocol of the disclosure uses biometrics to download encrypted, cloud-based vital health records in real time. In one embodiment, a first, second and a third level of encryption are used such that user medical data is triple-encrypted.

First responders and the city's hospital emergency medicine departments have one or more software applications described here installed on their mobile devices such as smartphones, tablets, computers, and other internet-enabled devices including, but not limited to MCTs, defibrillators, and telemetry devices, fingerprint scanners or other biometric scanners. When responding to a medical call, emergency responders and health care providers quickly scan the individual's fingerprint, such as within less than about 30 seconds or less than about 20 seconds, and retrieve the patient's name and any essential information provided (i.e., blood type, allergies, current medications, critical medical history). Rapid access to this vital information helps improve emergent care situations and reduces medical errors. At the same time, the system via a server communication or communication from the client application automatically will notify the patient's emergency contact person that first responders have initiated treatment and/or transport to a hospital.

Pharmacies and other points where medicines can be dispensed may also have the disclosed software on kiosks or other internet-enabled or networked devices with scanning capabilities to capture and transmit subscribers' up-to-date medicines. Pharmacy patient databases may be tethered to the private database behind the disclosed systems and methods to ensure real-time passing of current medications and dosage into patients' registered profiles. Upon a reasonable period of time after the expected completion of a course of the prescribed medication, that medication and its dosage information will be purged from the visible portion of the records that can be retrieved by the first responder or emergency medical personnel.

With permission from the subscriber/patient, payors (i.e. health insurance carriers) may also receive notification from the disclosed system to enable immediate initiation of claims processing. This may happen at the time of transport to the hospital or admission into the hospital. No clinical information will be passed via the system; only information about the patient being brought to the hospital will be shared. A meaningful identifier such as the insurance policy number will be used to identify the patient; no biometric-based identifier will be shared with the payors.

The use of the system and methods of the disclosure is completely voluntary. Users opt in and thus choose to participate and register their fingerprint. Each user then decides what information they want to include, and the user decides who has access to that information. Each user sets the parameters and permissions, and is the only person who can make changes or updates. In part, the disclosure relates to a retrieval tool that helps deliver the vital health information a user would normally share in an emergency to help treat their injuries.

The system and methods of the disclosure include a mobile implementation. They are designed to work with various mobile devices (smartphones, tablets, laptops, etc.), meaning first responders can pull up an individual's essential medical information anywhere at any time. The emergency data retrieval software can be installed on or otherwise ported for installation on any suitable mobile device, computer or operating system for such devices. The software includes backup networking functionality that allows a first mobile device to communicate to a second mobile device to establish a communication change when there are service outages in cell towers or other communication services. The mobile devices can also include a set of data for patients for all subscribers or all subscribers in an active area such that in the event of an outage the mobile device of a user such as an injured party or a first responder can retrieve the medical information and transmit it to other mobile devices that are running the emergency data retrieval software.

The systems and methods include various data security features. In some embodiments, there is no data stored on mobile devices themselves. All medical information is kept in the triple-encrypted private registry. In one embodiment, a fingerprint brings up an individual's profile the same way a mobile device loads a webpage—only faster because the system's data demand is negligible. Individuals' records are compressed, and secure. Also, the discreet database is separate from private/public health system records in order to ensure the impermeability of the servers housing the database. In one embodiment, a compressed, full or regional version of the subscriber database is stored on the mobile device. In one embodiment, the subscriber data or a portion thereof and the associated medical records are stored on a SIM chip or another form of persistent memory of a mobile device, such that the data remains available in the event of an operating system reinstall or loss of service to the mobile device's communication network.

In part, the present disclosure relates to systems, methods, and devices for using biometrically secure remote authentication for access to electronic databases. In one embodiment, the systems and methods provide real-time, biometrically-secure essential health information to first responders without any hardware, such as a bracelet, pendant, or other device or visual identifier such as a sign or badge required by the patient.

In one embodiment, subscribers are assured that life-saving information is available to first responders and emergency medical personnel at any time.

Various embodiments of the disclosure relate to remote data collection from one or more members of a population using a mobile device and biometric parameters to anonymize the data collection process. These different embodiments represent a remote identification process that is applicable to counseling and collecting data from a population of interest. As a result, certain of the embodiments of the disclosure relate to remote identification or ("Remote ID") technology. Once collected, a set of anonymous data can be used to generate reports and perform statistical analysis relative to an anonymous or partially anonymous population of interest. Suitable reports include, but are not limited to, infection distribution, geographic distribution of a user characteristic, census data collection, population estimates, and others.

Suitable mobile devices that can perform the data collection, data transmission, and biometric parameter collection processes associated with Remote ID technology include smart phones, desktop computers, personal digital assistants (PDAs), laptops, and other portable or substantially portable electronic devices configured to send and receive information. In one preferred embodiment, information that includes patient data associated with a biometric identifier is wirelessly transmitted from a user location to a remote database or remote processing location. That patient data can be used to track an individual's health and treatment regimen by enrolling the patient in a database by which a biometric identifier is used to query the same database and retrieve the patient's anonymous file.

Further, in one general embodiment, the present disclosure relates to systems, devices, and methods for using secure biometric parameters to remotely access electronic databases. In one embodiment, the methods, devices, and systems described herein can be offered in conjunction with a disease test kit, such as an HIV test, or other kit amenable to use when collecting data from members of a population of interest. By pairing a diagnostic kit or disease test with the system, methods, and devices used to counsel members of a population and collect personal, yet anonymous, information, it is possible to increase the number of tested, treated and tracked individuals as well as the commercial sales volume of such tests or kits.

In one general embodiment, the disclosure relates to a method of remote data collection and remote user identification. The method is implemented using a computer. The method includes the steps of providing a mobile device that includes a biometric scanner, memory, a display, and a processor; acquiring a biometric identifier from a member of a population of interest using the biometric scanner; collecting personal data from the member of a population of interest; transmitting the personal data; and storing the personal data such that it is indexed using the biometric identifier. The mobile device can be selected from the group consisting of a laptop, a personal digital assistant, a smart phone, a messaging device, or other devices.

The biometric identifier can be selected from the group consisting of a fingerprint, a retinal scan, or other personal identifier suitable for scanning and electronic transmission and storage. In one embodiment, the member of a population of interest is an anonymous member of a population of interest. In one embodiment, the method also includes the step of anonymizing the personal data. In one embodiment, the method also includes the step of searching a database that comprises anonymous personal data associated with enrolled members of a population of interest in response to transmission of a fingerprint of an enrolled member. Further, in one embodiment, the method also includes the step of generating a report relative to an anonymous population of interest, each anonymous member of the population of interest having a data file and biometric identifier stored in a database.

In one general embodiment, the disclosure relates to a mobile device-based individual data collection and transfer system. The system includes a mobile device, the mobile device comprising a transmitter, a receiver, a processor, and a data entry interface; and a biometric scanner, the scanner in electronic communication with the mobile device, the processor for receiving biometric data from the biometric scanner, the processor receiving anonymous personal data generated using the data entry interface, wherein a biometric identifier is generated using the scanner and paired with a set of personal data collected using the mobile device such that the set of personal data can be stored anonymously at a remote location. In one embodiment, the system can include a diagnostic test kit for generating test results such that the test results include an element in the set of personal data. In one embodiment, the system can include an anonymizing module that executes using the processor that processes user data and restricts the transmission of personal identifiable information.

In one general embodiment, the system can further include a server and a database, the server comprising software that enrolls members of a population of interest in response to a biometric identifier received from the mobile device, the database storing a plurality of member files, each member file associated with a unique biometric identifier. In one embodiment, the database is searchable using biometric identifier templates of anonymous members of a population of interest. In one embodiment, a user's template is derived from or relatable to a biometric measured user feature such as a scan of a fingerprint, but the template does not include an image or the data associated with the scan. This provides an increased level of security. Further, in one embodiment, the data entry interface is programmed to display fields and receive inputs specific to a data collection scheme, the data collection scheme selected from a group consisting of baseline education surveys, user registration, concert admission, medical data collection, census data collection, HIV screening, user enrollment, and data collection relating to a population of interest with sensitive information that requires confidential storage.

In one general embodiment, the disclosure relates to a method for anonymously collecting information from a member of a population of interest. The method includes the steps of acquiring a biometric identifier from an anonymous member of a population of interest using a biometric scanner; anonymously collecting personal data from the member; associating the member's biometric identifier with the member's personal data; anonymously transmitting the personal data; and storing the personal data such that the personal data is indexed using the biometric identifier such that the personal data remains anonymous. In one embodiment, the personal data does not include information about the member's personal identity. The method can further include the step of searching a database that comprises the personal data in response to transmission of a biometric identifier of an enrolled member.

In one general embodiment, the disclosure relates to a computer system for anonymously collecting information from a member of a population of interest. The computer system includes an electronic memory device; and an electronic processor in communication with the memory device, wherein the memory device comprises instructions that when executed by the processor cause the processor to: convert a biometric identifier acquired from a member of a population of interest into a template; associate the template with anonymous personal data collected from the member; and transmit the anonymous personal data to the electronic memory device. In one embodiment, the memory device includes instructions that when executed by the processor cause the processor to execute an anonymizing module that processes user data and restricts the transmission of personal identifiable information.

In one embodiment, the system includes a server and a database, the server comprising software that enrolls members of a population of interest in response to a biometric identifier received from the mobile device, the database storing a plurality of member files, each member file associated with a unique biometric identifier. Further, in one embodiment, the database is searchable using biometric identifier templates of anonymous members of a population of interest.

In one general embodiment, the disclosure relates to one or more tangible computer readable media encoded with software, the software comprising computer-readable instructions operable, when executed, to cause one or more processors to: convert a biometric identifier acquired from a member of a population of interest into a template; associate the template with personal data collected from the member, the personal data being anonymized such that the member's identity is not transmitted with the personal data; and transmit the personal data to the electronic memory device. In one embodiment, the software includes computer-readable instructions operable, when executed, to cause one or more processors to execute an anonymizing module that processes user data and restricts the transmission of personal identifiable information.

All of the proceeding embodiments can be combined together individually or in the aggregate and all such embodiments are within the scope of the disclosure. In addition, all methods and techniques described herein can be implemented as stand-alone methods or as a processor-based system or method. In one embodiment, such a system includes an electronic memory device; and an electronic processor in communication with the memory device, wherein the memory device comprises instructions that when executed by the processor cause the processor to execute one or more of the method steps described herein.

The system and related methods enables one-click, real-time incident alert and transport update to emergency contact (initiated by medical personnel via the subscriber's profile). This alert system is able to transmit info via SMS, email, phone. The entire system is optimized for mobile devices.

In part, the disclosure relates to a real-time mobile service, implemented using software and a biometric scanner, that enables first responders and emergency medical staff to access patients' (subscribers) essential health information using only the patient's fingerprints to retrieve what subscribers have chosen to share.

There are various roles or actions available to a subscriber. Some exemplary subscriber actions include: Chooses to enroll, Registers his or her fingerprint at a designated point of service, Decides what information to include, Enters info personally into a simple web-based registration interface, and Sets access permissions. In one embodiment, the subscriber is the only person with authority in the software that can make changes or updates to this information. There are various roles or actions available to a user. Some exemplary user actions include Opens the app on mobile device, Scans patient's fingerprint, Automatically retrieves subscriber-provided vital health information, and Automatically notifies & updates subscriber's emergency contact, PCP, and insurance.

In part, the disclosure relates to computer system for securely retrieving remotely stored data for an individual having a medical emergency. The system includes an electronic memory device; and an electronic processor in communication with the memory device, wherein the memory device comprises instructions that when executed by the processor cause the processor to: store medical information for an enrolled user subscribed to emergency response service in a data storage device at one or more remote locations; store biometric identifier for the user subscribed to emergency response service at one or more locations; correlate biometric information and medical information on a per user basis; and transmit the medical information to the first mobile device in response to receiving an aggregate identifier generated in response to a scan of the enrolled user.

In part, the disclosure relates to a method of securely retrieving remotely stored data for an individual having a medical emergency. The method includes storing medical information for an enrolled user subscribed to emergency response service in a data storage device at one or more remote locations; storing biometric identifier for the user subscribed to emergency response service at one or more remote locations; correlating biometric information and medical information on a per user basis; retrieving the medical information using a first mobile device in response to input a scan of the user using a first software application running on the first mobile device; and displaying the retrieved medical information on the first mobile device.

In one embodiment, the method includes the step of contacting emergency contact of user when user is scanned by emergency response personnel to generate a biometric identifier and biometric identifier matches the biometric information of the user. In one embodiment, the biometric identifier is a string of a plurality of characters. In one embodiment the method includes generating the biometric identifier, wherein the step of generating the biometric identifier comprises adding a client code to the string to generate an aggregate code and then hashing the aggregate code to generate the biometric identifier.

In one embodiment, the aggregate code includes a unique user identifier (UUID), the UUID added to the client code and the string. In one embodiment, the method includes the step of accessing a central prescription database; identifying active prescriptions; and including the active prescription in the medical information.

In one embodiment, the first software application is stored in a SIM card of the first mobile device. In one embodiment, the first software application controls one or more network protocols installed on the first mobile device, wherein the network protocols support direct communication between the first mobile device and a second mobile device during a telecommunication network service provider outage.

In one embodiment, the method includes generating one or more alerts based upon frequency of the user's calls or appointments with healthcare providers exceeding an alert threshold. In one embodiment, the method includes generating one or more alerts based upon frequency of the user's prescriptions being written or category of prescriptions, wherein the category is selected from the group consisting of pain medication, antidepressants, stimulants, and schedule II medications. In one embodiment, the medical information is selected from the group consisting of allergies, active medications, prior medications, vital or acute medical history, name, age, gender, blood type and date of birth.

In one embodiment, the method includes downloading a secure file containing one or more profiles of subscribers to a local device on a predetermined schedule to generate a local truncated set of medical records based on subscriber location. In one embodiment, the method includes the step of accessing a third party source of data; retrieving updated information from the third party source of data and updating the medical information using the updated information.

In one embodiment, the system includes instructions to cause the processor to access a third party source of data; retrieve updated information from the third party source of data and update the medical information using the updated information. In one embodiment, the system includes instructions to cause the processor to generate the biometric identifier, wherein the step of generating the biometric identifier comprises adding a client code to a template to generate an aggregate code and then hashing the aggregate code to generate the biometric identifier.

In one embodiment, the system includes instructions to cause the processor to run one or more application servers, the one or more application servers running an emergency data retrieval software application. In one embodiment, the system includes instructions a first database to store session information comprising one or more aggregate identifiers. In one embodiment, the system includes instructions a second database to store one or more subscriber records, the subscriber records comprising a set of one or more sensitive pieces of medical information.

BRIEF DESCRIPTION OF THE DRAWINGS

Various embodiments and other aspects of this disclosure will be readily apparent from the detailed description below and the appended drawings, which are meant to illustrate and not to limit the disclosure, and in which:

FIGS. 3A-J are a series of exemplary screenshots of user sign in, fingerprint scanning, record retrieval, and patient counseling, in accordance with various embodiments of the present disclosure.

FIGS. 4A-D are a series of screenshots showing exemplary user interfaces relating to patient identification screens, as well as pre-test, screening, and post-test questionnaires in accordance with an embodiment of the disclosure.

FIG. 12A-12F are schematic diagrams of various mobile devices and exemplary interfaces, medical data, and features.

DETAILED DESCRIPTION

Figure 1A:
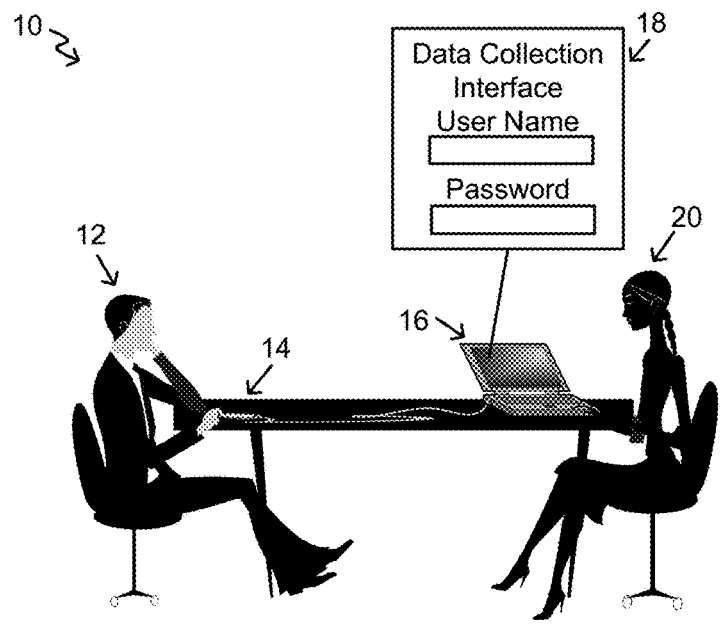
FIG. 1A is a diagram of a system user counseling a member of a population of interest and signing in to a data management system, in accordance with an embodiment of the disclosure.

Before explaining the disclosed embodiments in detail, it should be noted that the disclosed embodiments are not limited in application or use to the details of construction and arrangement of parts illustrated in the accompanying drawings and description. The disclosed embodiments may be implemented or incorporated in other embodiments, variations and modifications, and may be practiced or carried out in various ways. Further, unless otherwise indicated, the terms and expressions employed herein have been chosen for the purpose of describing the illustrative embodiments for the convenience of the reader and are not for the purpose of limitation thereof. Further, it should be understood that any one or more of the disclose embodiments, expressions of embodiments, examples, can be combined with any one or more of the other disclosed embodiments, expressions of embodiments, and examples, without limitation.

The following description refers to the accompanying drawings that illustrate certain embodiments of the present disclosure. Other embodiments are possible and modifications may be made to the embodiments without departing from the spirit and scope of the disclosure. Therefore, the following detailed description is not meant to limit the present disclosure, rather the scope of the present disclosure is defined by the claims.

In various physical and social sciences, field researchers, medical practitioners, and other data collectors are often limited to data contained in their own written records, on their own computer hard drives, or on remote databases requiring both an Internet-enabled connection and electricity. With confidentiality a growing concern as the use of electronic databases increases, the need for security has become urgent in various data collecting scenarios. Further, in light of user sensitivity to the dissemination of personal information, there need to be safeguards to anonymously obtain data while facilitating follow-on research and interactions with the anonymous provider of the data. In the case of a data providing user or subpopulation member that is seeking treatment, such as alcoholics, AIDS patients, drug users, and others with sensitive conditions, the need for anonymously enrolling users while enabling identification of the anonymous users is great.

In addition, during emergency crisis management, such as a train derailment, car crash, terrorist event or other incident or MCI, providing a system and associated data retrieval software for use with mobile devices to securely retrieve medical information and transmit information about the incident is of great value. With such a system, users, subscribers, and emergency points of contact can receive the relevant information about an incident involving a first user upon a biometric scan of the first user. In addition, when medical personnel such as first responders scan a user they can learn if the user has extenuating factors relevant to forming a treat/no treat decision such as a history of excessive prescription requests, excessive pain killer prescription, repeated emergency calls or other factors. Such factors and others can be indicative of a substance abuser or an attention seeker rather than a person in need. A subscriber's insurance status can also be provided to the first responder. The software can generate alerts based on historical information to flag such questionable incidents so that the first responder can make an informed treatment decision.

Those seeking to use electronic databases in remote locations are often at a disadvantage because in much of the world there is no direct access to electricity or the Internet. However, there is wide penetration of cellular signals. Cellular signals can be used to transmit and transfer electronic information. Yet even with seemingly secure cellular data transfer, traditional data is not always secure and can become compromised. The features relating to using backup communication gateways such as USSD gateways and applications and data for emergency record retrieval being stored on a SIM card or other persistent memory device are additional benefits of the disclosure. These features help ensure the necessary medical information and records are available in the event of communication outages which can occur generally or as part of a MCI.

At a general level, the disclosure relates to remote identification of members of a population of interest such that confidential personal data associated with one or more of the members can be collected and stored in a secure manner. In some embodiments, the data is securely transmitted to one or more central databases. In some embodiments, the disclosure provides a mobile, biometrically-secured confidential access system designed to permit controlled access to medical records from anywhere there is a cellular signal, a data transmission network, post for mailing disks, and/or internet access. In particular, the system is ideally suited to use in extremely rural or remote areas where lack of electricity is an impediment to creating, accessing, and maintaining electronic medical records. The embodiments described herein provide for security and confidentiality with respect to the personal data for a given member of a population of interest. In some embodiments, fingerprints are used as the only identifier for certain database records, such as certain "front end" records. Thus, a member of a population is treated (or otherwise interacts with the system) anonymously, although counterintuitive, by using a personal biometric identifier in lieu of a name or government issued identifying number.

In one embodiment, the disclosure allows for the anonymous collection of information from a subject (e.g., a patient) or a group of subjects (e.g., HIV patients or drug users). Specifically, rather than providing a name, social security number, or other personal identification, a subject instead provides a biometric identifier, such as a fingerprint, which is associated with that subject's file. The subject's name or other identifying information may never be provided and, if provided, is not associated with the biometric identifier. Thus, the subject's identity remains anonymous and independent of the biometric identifier.

Using a biometric identifier in this way is akin to assigning a random identifier to the subject. However, a biometric identifier has significant advantages over a random identifier (e.g., a number, bar code, wristband, RFID, etc.) since a random identifier can be easily lost, misplaced, forgotten, damaged, or misappropriated. By using a biometric identifier, the subject necessarily brings the requisite authentication to every consultation, thereby permitting seamless and anonymous updating of the subject's file. Moreover, since subject names or other personal identifiers are not necessary, valuable data (e.g., demographics, health status, prevalence of substance abuse, response to treatment) can be distributed to third parties (e.g., researchers, health care providers) while maintaining complete subject anonymity.

Thus, as an example, if the population of interest includes people in a remote location that may be suffering with HIV, a mobile device with a biometric scanner can be used to collect data from the population of interest and relay that data via a wireless link to a remote database. Further, the recorded personal data can be mined/used/analyzed by designated researchers from a "back end" perspective without compromising the anonymity and confidentiality of the members of the population of interest. If the population of interest includes drug users, single mothers, adopted children, homeless people, clinical trial participants, criminals, or other classes of individuals, personal or cultural barriers of confidentiality and security can make people unwilling to cooperate or volunteer personal information. The present disclosure overcomes many data collection issues and allows health care workers to anonymously collect information, treat, and track individuals, and gives researchers an opportunity to access larger pools of data.

In FIG. 1A, an implementation of the method and the associated system and devices suitable for collecting personal information and a biometric identifier at a remote location is shown. Specifically, as shown in FIG. 1A a health care worker, shown on the right, is counseling a member of a population of interest (such as a patient) on the left. In some embodiments, after a health care worker signs in using encrypted password, the patient places his fingerprint on a USB fingerprint scanner, which then displays the image in a browser-based window. The user "submits" the image of the fingerprint embedded in the URL via the Internet generally via a device connected to a cellular phone network or other network (e.g., using a smart phone or cellular modem, network interface device or wireless data card inserted into or connected to a laptop computer). The remote/central server, using the present disclosure, searches through the already captured fingerprint image/medical record database for a match. If a match is found, the patient history (or other information in an enrolled user's file or fields) is displayed back as a URL-based record. If no match is located, the user enrolls the patient's fingerprint as a new record in the central database and is ready to create new fields of data relative to screenings/visits/etc.

At future appointments, once the patient "signs in" to the system with his fingerprint, health care providers can access the patient's medical history by clicking on previous appointment dates. In one embodiment, these clickable dates are functionally URLs that connect to the data collected on the previous appointment.

In general, embodiments of the disclosure use various communication protocols and networks to collect certain categories of data associated with, resident on, captured using, or otherwise generated by a user's mobile device or a substantially mobile device, such as a desktop computer. In addition, embodiments also relate to the use of any type of data that is processed remotely in response to data sent from the mobile device. As a result, the embodiments of the disclosure relate to any type of data suitable for use by mobile devices and processors. The data can include, but is not limited to any suitable type of data such as metadata, personal data, device-generated data, user-generated or inputted data, and various types of derived data, all of which may be the same, different, or overlap with respect to data type in some embodiments. In one preferred embodiment, the data of interest is personal data associated with a patient suffering from a disease or condition.

The advantages of the present disclosure include, without limitation, that it is portable, easy to transport, and provides electronic access to confidential data through various access and searching mechanisms. It is straightforward to move and utilize devices that implement Remote ID technology anywhere on Earth where there is access to the Internet or cellular telephone signal.

An existing individual record may be queried by launching the client application, presenting a fingerprint, a template associated with a biometric identifier, or other biometric scan and having the server retrieve a matched record and display/transfer it to the remote client.

Various embodiments provide access to individual or aggregated records through one or more query/search functions. In one embodiment, an authorized user may select a function within the client or server application that requests the export of a specific record or range of records that meet user-entered search criteria (for example, contents of specific fields, ranges of values in specific fields, as examples.) In another embodiment, an authorized user may request an export of all or specified records, ranges of records, etc., into an extant database application such as Oracle, SAP, MS Access, MySQL, etc., or statistical analytics application such as SPSS, JMP, etc.

Figure 1B:
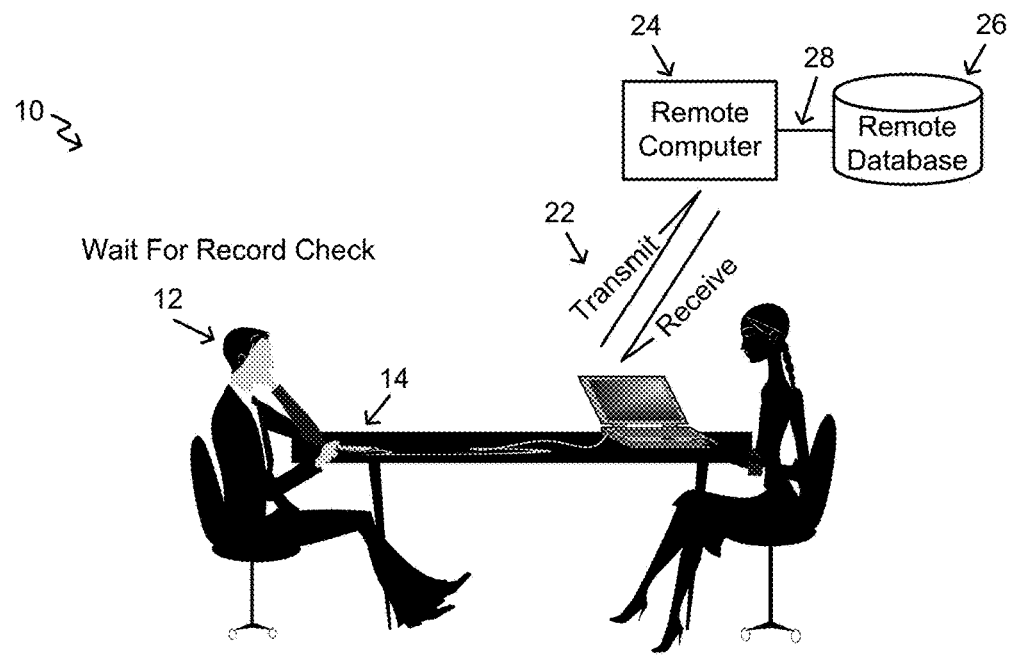
FIG. 1B is a diagram depicting data transfer between a local computer and a remote computer and/or remote database, in accordance with an embodiment of the disclosure.
Figure 1C:
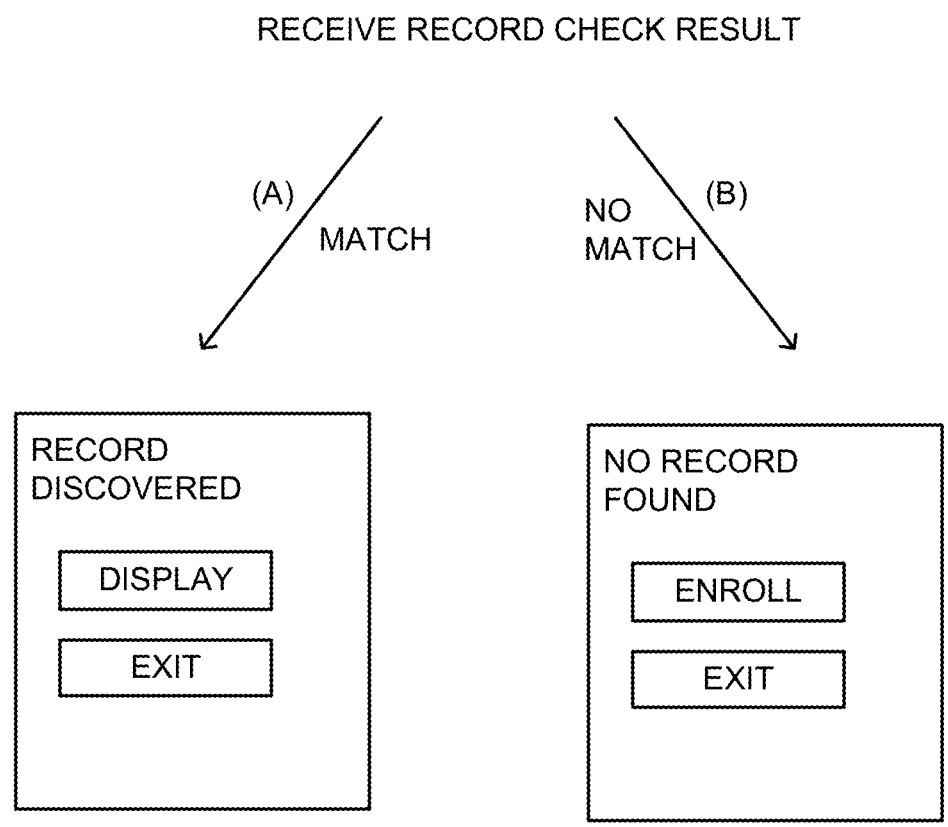
FIG. 1C is a flowchart of a record check result, in accordance with an embodiment of the disclosure.
Figure 2:
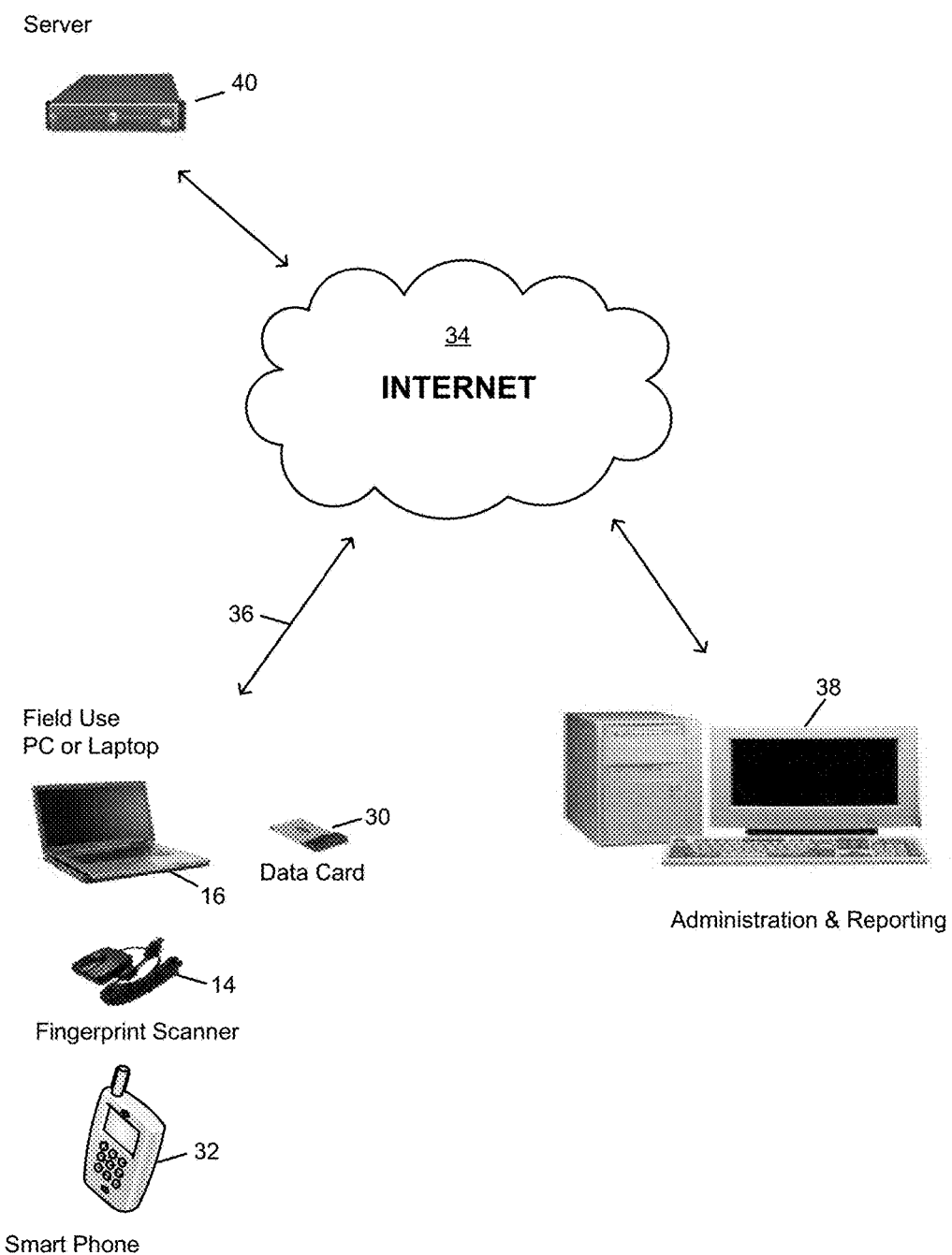
FIG. 2 is a diagram of a network-based system, in accordance with an embodiment of the disclosure.

Referring to FIGS. 1A to 2, there is shown how an exemplary anonymous Remote ID system 10 works in a real world enrollment or data collection scenario, in accordance with an illustrative embodiment of the disclosure. In FIG. 1A, an encrypted local computer, smart phone or other suitable mobile device 16 requires authentication by an authorized user (e.g., a researcher, doctor, health care worker) 20 using, for example, a user name and password are received by an interface 18. The mobile device, such as a laptop 16, is in communication with a biometric scanner (e.g., a USB fingerprint scanner, built in scanner, or other scanner) 14. Once the user 20 has signed in, the patient (or member of a population of interest) 12 provides a biometric identifier, such as a fingerprint, to the biometric scanner 14. The present disclosure, using the biometric identifier, associates the patient's biometric identifier with the patient's medical information located in a central database. In some embodiments, the user 20 collects medical information from the patient before or after the patient provides a biometric identifier. In other embodiments, the user can retrieve patient information which was previously collected when the patient was enrolled or at a time after enrollment. Thus, the patient's biometric identifier can be used to create, store and retrieve the patient's personal information from the encrypted local computer or from a remote computer or database. Software, programmable logic or other types of computer instructs are resident in memory in the devices 22, 24 shown in FIG. 1B to capture, transmit, and process the relevant biometric data and user 12 records.

FIG. 1B shows communication of information 22 between a local computer 16 and a remote computer 24, in accordance with an illustrative embodiment of the disclosure. The remote computer 24 can be in further communication 28 with a remote database 26 which stores personal data, such as patient medical information and/or makes it available to system users.

FIG. 1C shows a flow chart of a patient record check, in accordance with an illustrative embodiment of the disclosure. After the patient provides a biometric identifier, the computer then searches the database (either local or remote) for a matching biometric identifier already on file. If a matching record is discovered, the user is given the option of displaying the patient's record or exiting from the system. If a matching record is not found, the user is given the option of beginning the patient enrollment process (creating a new record in the database) or exiting from the system.

When results of the biometric identification reveal that a patient is a new patient (i.e., previously unenrolled), a new patient screening session is created. In one embodiment, creating a new screening session includes the step of entering data into each form in order (pre-screening questionnaire, screening and post-screening questionnaire).

FIG. 2 shows an exemplary computer system in greater detail. A suitable mobile device 16, such as a field use personal computer, smart phone, or laptop, is in communication with a biometric scanner 14, such as a USB fingerprint scanner, which is used to obtain a unique biometric identifier from a patient. The mobile device can include a data card 30 or other storage device for locally storing information, such as patient records. In one embodiment, a smart phone 32 with a built in biometric scanner can be used to perform remote and anonymous data collection with respect to a population of interest. In one embodiment, a diagnostic test kit (not shown) is also used to collect information that is then stored anonymously.

In addition, the mobile device can also be capable of connecting to the Internet or a network 34 using a wired or, more preferably, a wireless 36 connection. Through the Internet and/or network 34, the mobile device 16 is able to communicate with other computers or secondary mobile devices. For example, the mobile device can communicate over the Internet 34 with an administrator 38 for processing and reporting purposes. The database and the relevant programmable logic or software modules to facilitate the Remote ID process and other processing and data display steps can be resident on the administrator computer 38 or the server 40. The mobile device can also connect to server 40 (e.g., a Windows based server), such as a data server or another computer to upload or download patient records.

Figure 3A:
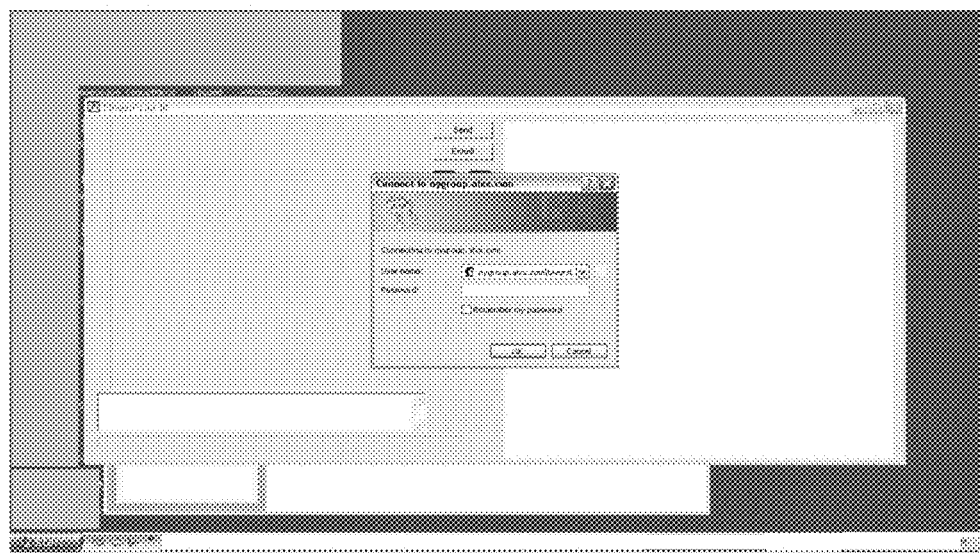

FIG. 3A shows an exemplary login screen displayed on the mobile device, in accordance with an illustrative embodiment. To authenticate (i.e., sign on) to the system, a user enters a username and password to access the system and pass through the first level of security. The mobile device transmits the patient's biometric data by, for example, a URL to a remote server and the remote server retrieves any matching records and displays the records on the mobile device. Because, in one embodiment, the patient's biometric identifier is used to identify the patient's records, the patient's name and social security (or other patient specific identifier, index, or tracking device) number are never displayed because no personal identifiers other than gender and year of birth are taken. If no records match the patient's biometric identifier, the user is given the option of creating a new record in the database, i.e. enrolling the patient.

Hardware/Software Components

In various embodiments, reference is made to a workstation, as used herein the term is interchangeable with any mobile device or fixed device (or combination of devices or subsystems) suitable for capturing information from a member of population of interest and generating a biometric identifier associated with such member (or user). In one preferred embodiment, the workstation is a computer, smartphone or a laptop that is in electronic communication with a biometric scanner.

The workstation (remote mobile device or data capture device) and central server applications can be programmed and ported between various commercial and publicly available programming languages. Alternatively, certain features of the remote identification described herein can be implemented using an application specific integrated circuit. One embodiment described herein is written in Borland's Delphi incorporating function calls to Griaule Biometric's Fingerprint SDK. Other embodiments can use Griaule's Linux SDK, VeriFinger Linux SDK and others. Various other biometric identifier specific SDKs can be used as appropriate to collect fingerprints and other identifiers for use with the systems and methods described herein. However, other biometric software, middleware, open source software, freeware and SDKs can be used in various embodiments. The Griaule code performs the scan to image, image to vector and vector compare functions. In one embodiment, as used herein the term "vector" refers to any matrix or array of data. In another embodiment, the term "vector" refers to mathematical relationships between points and the paths connecting them to describe an image. Thus, in one embodiment biometric identifiers are imaged as vector graphics that include one or more paths (or the points that form such paths).

In one embodiment, the other aspects of the application are either performed by the Delphi code (or other applications or software modules) or by using web based PHP scripting. In one embodiment, there are two distinct software applications; one for the workstation and one for the server. Certain features of these programs are described below.

In one embodiment, the workstation or mobile device includes or otherwise interfaces with an anonymizing module resident in local or remote memory storage that executes using a processor included within the mobile device that processes user data and restricts the transmission of personal identifiable information.

The Workstation/Mobile Data Capture Elements

Comprising a Windows (XP, Vista, 7, Mobile, CE) or Linux operating system based PC or other remote device, such as a Smartphone, tablet or PDA running under various mobile operating systems such as: Windows Mobile, Symbian, Linux, Palm, or WebOS, a fingerprint (or other biometric) scanner and customized Remote ID workstation application, the workstation is used to capture, insert, retrieve and edit data from a server based on the identified fingerprint (or other biometric identifier). The workstation application scans and captures a fingerprint or other biometric identifier, determines the quality of the scan (allowing for rescanning if the scan is not optimal), converts the fingerprint or biometric image to template and sends the template to one or more servers via an Internet connection.

If the server application finds the fingerprint, biometric identifier, or scanned template in the database, the database record is opened and appropriate information is returned to the remote workstation to view or edit. If the server application fails to find the scanned template a new template and record can be added to the server's database. In one embodiment, the scanned template is a vectored template that includes a digitized vector image of the biometric scan. In another embodiment, the reference to a vector refers to a row, column, or other m by n array or matrix that encodes numerical data that is correlated with a biometric identifier. Operation of the workstation typically includes a mobile device, a biometric scanner, and Internet connectivity (laptop cellular modem Wi-Fi, etc.).

Remote or Local Server/Remote Data Storage and/or Processing

In one embodiment, fingerprint or other biometric template and form data reside on a central server. When a workstation connects to the server and sends the fingerprint or biometric identifier (or an associated template) the anonymous remote identification server application searches the database for a match. If a match is found, the workstation is sent the appropriate information associated with the anonymously identified records. If no match is found, the workstation user has the option of creating a new database record, e.g. enrolling the new data. The server can be run on, by way of non-limiting example, Windows 2000, Windows 7, XP, Vista, 2000 Server, 2003 Server or any derivative. Typically, it runs on a web server (IIS, Apache, etc), PHP and has a persistent Internet connection. In the present embodiment, the data is maintained in a Microsoft Access database, but can be migrated to any ODBC compliant database application or system.

Additional details relating to the operation of an exemplary system implementation are provided below as a collection of exemplary method steps. The method steps need not necessarily be performed in the sequence recited below. In one embodiment (using fingerprint scan as the biometric identifier), the sequence of user events or software events may include some or all of the following steps:

1. An Internet connection is established.
2. A software application or module is executed.
3. A software application or module connects to the central server's web server or other application of interest.
4. User is required to log on using a secured log-on and password.
5. The main software application page is displayed.
6. When a finger is presented to the scanner, the finger is scanned and the fingerprint appears on a display along with a quality indicator (red=bad, yellow=marginal, green=good). The Griaule SDK performs the scan and creates a fingerprint template. It also returns the scan quality value that is converted to a simple displayable color indicator by the software application or module.
7. The finger can be rescanned until a good scan is obtained by simply removing the finger and re-presenting the finger in the scanner.
8. Once an acceptable scan is obtained, the user presses the Send button, initiating the transmission of the vectored template to a remote or local server.

9. The workstation waits for a response from the remote or local server.
10. The server accepts the connection, receives the template and compares it against the templates in the database. If a match is found, the server sends the workstation a unique ID for the matched record. If a match is not found, the server responds with a 'not found' code.
11. If the server responds with a 'not found' code, the workstation then connects to a server's web server and opens an Enroll page allowing the user to add the new fingerprint (scanned template) and associated data to the server's database.
12. If the server responds with an ID (such as existing database record, data set, or file), the workstation requests the detailed data page for that individual whose fingerprint (scanned template) matched.
13. Once the transaction is complete and the workstation has received a response from the server, the workstation disconnects from the server.

At this point, the user can navigate throughout the identified individual's data using a web-based interface, such as browser, terminal, client, or other suitable interface. The structure and content of the stored data can be customized for the specific application. One application is for HIV screening where the database contains questionnaire responses, HIV test results and demographic information. Patient anonymity is maintained because the system uses the fingerprint scanned template for identification and no other identifiable information (name, address, etc.) is necessary. As a result an anonymizing step is performed in the course of collecting data from certain populations of interest. In another embodiment the anonymizing step is automated such that algorithms or data routing is used such that even if personal information is collected along with the biometric identifier, such information is separated from the data or processed in a manner such that only certain users have access to such personal identifiers.

Since the fingerprint scanned template (or other biometric identifier) and the web-based forms database scripting are segregated, both the workstation and server applications can be customized for any use where biometric identification is desired (or necessary) to create or maintain database information. In one embodiment, a Delphi-based application, a Java-based application, or another software module is used for obtaining a fingerprint (such as with a scanned template) as data (using the workstation), sending the fingerprint (as data or a scanned template) using a workstation and searching fingerprints in the form of a collection of scanned templates (or other indexed data) stored at a remote server while the PHP/web interface uses the identification from a software application, such as a Delphi application, Java-based application, etc. to store and retrieve data in the database. In one embodiment, once a fingerprint/biometric identifier (scanned template) has been identified the PHP/web interface manages whatever data is desired to be stored.

Thus, in one embodiment, since no data is permanently stored on the local workstations, this arrangement significantly reduces the risk of loss or exposure of personal data. The exception to this occurs when, upon the workstation's lack or loss of an Internet connection of any type, the workstation automatically executes an 'off-line' mode, which permits the workstation to capture and store both the scanned template and associated acquired data, which are then automatically transmitted to the central server and deleted from the workstation upon re-establishment of any Internet connection.

In addition, in other embodiments report generation and other types of reporting functionality and data mining modules are part of the system and method embodiments. The reporting features of the disclosure are integrated with the functionality of the database. The present embodiment includes methods, processes, and programming for authorized users to search and query the created database(s) to create and retrieve report(s) generated by interaction between a workstation device and the server, such that the data can be retrieved from any to all individual records based upon the query criteria. One example of a report showing information collected using Remote ID technology for a population of interest is provided below as Report Example I.

In part, the present embodiment includes a 'query template generation' function, permitting an authorized user or administrator to create and/or save a specific set of criteria. Those criteria may be any single or combination of named or otherwise identified fields included in the database. For example, using the present illustrative embodiment, a researcher evaluating the efficacy of a specific educational or medical intervention can create a query and generate a report based upon any or all individual patients who participated in an interventional HIV program and the results of each subsequent HIV test. The present embodiment, and, more generally, any embodiment of the disclosure, permits the authorized user to name and save the report to a specified server location or to the connected workstation device and then, using standard analytic tools, apply statistical methodology to the reported data, in the present example, to assess potentially differentiable outcomes of the interventions.

Exemplary Screen Shots/Graphic User Interface Embodiments

Various aspects of the disclosure can be understood relative to certain screen shots and graphic user interface displays. An exemplary collection of such screen shots and interfaces follow. Although in this illustrative embodiment the screenshots reference HIV testing, these are but exemplary templates and can be configured for anonymously enrolling new individuals and securely storing and retrieving information for various other populations of interest.

Referring to FIG. 3A, an exemplary login screen is shown. To authenticate (i.e., sign on) to the system, a user enters a username and password to gain access to the system.

Figure 3B:

Referring to FIG. 3B, an exemplary opening screen is shown. A user is asked to log in prior to arriving at this page. The left side of the workstation application is a window to the Griaule SDK that, in this embodiment displays the fingerprint scan, while the right displays data via a web interface from a processor-based device, such as a server. One exemplary server is a central server that is programmed with or has remote identification software installed that can receive biometric data and query a database of enrolled members while being able to enroll new members and perform analysis relating to the underlying data. In one embodiment, data analysis can be performed at a workstation remote from the server by running statistical software packages relative to an anonymous data set collected from a population of interest to generate social, medical, treatment, disease trajectory, and other reports of interest.

Figure 3C:
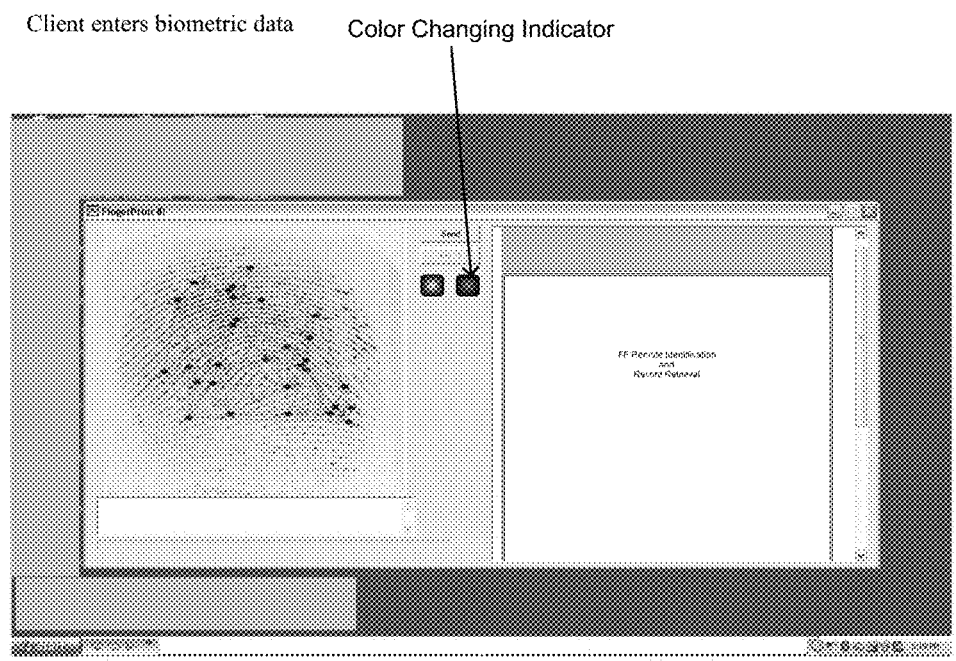

FIG. 3C shows an exemplary fingerprint scan. When a finger is presented to the fingerprint scanner, the Remote ID software creates a vectored map (template) of the scanned image. Here, the process of vectorizing the image is performed by the Griaule SDK. Specific points in the image are identified and their relative position measured and documented. The higher the detail present in the image, the more points in the image that can be identified. The client application can be configured to the specific number of biometric reference points desired; the greater the number of reference points, the more unique or discrete the record. The program can be configured to indicate whether or not an acceptable quality fingerprint scan has been obtained.

Figure 3D:
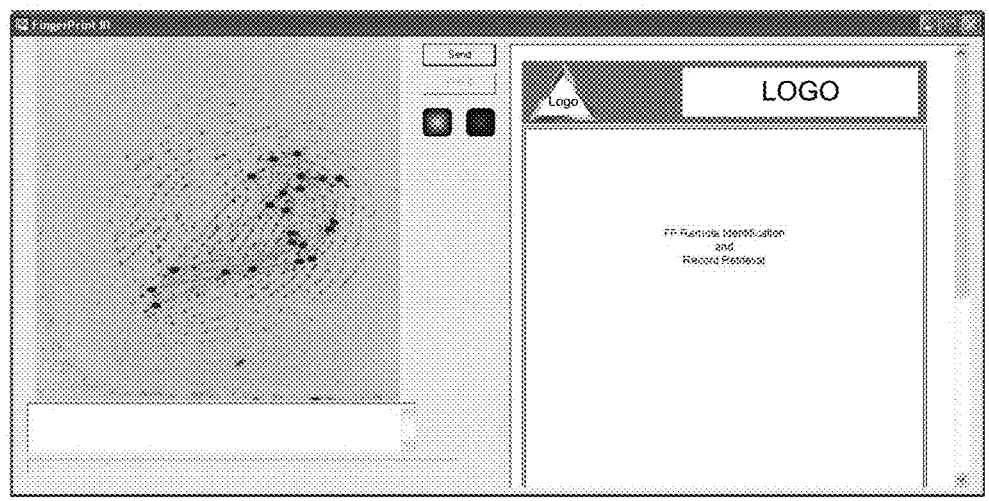

For example, FIG. 3C shows that the fingerprint scan was acceptable by the color changing indicator in the center column. As shown in FIG. 3D, an indicator in the center column indicates a poor scan and is considered unacceptable to submit for a match search. In one embodiment, such a match search or matching query is performed using a local or central database. A color changing indicator or symbol will be displayed when a scan is marginal but allowable.

A finger scan can be repeated as easily as removing the finger from the scanner, then presenting to the scanner again. When a good scan is achieved, the data can be sent to the Remote ID server for matching. The Remote ID application will transmit the scanned fingerprint template data created by the Griaule SDK to the Remote ID server in response to clicking on the SEND button in the center column of an interface displayed using the workstation application. As is the case throughout the embodiments described herein, various interface details are provides as non-limiting examples.

Figure 3E:
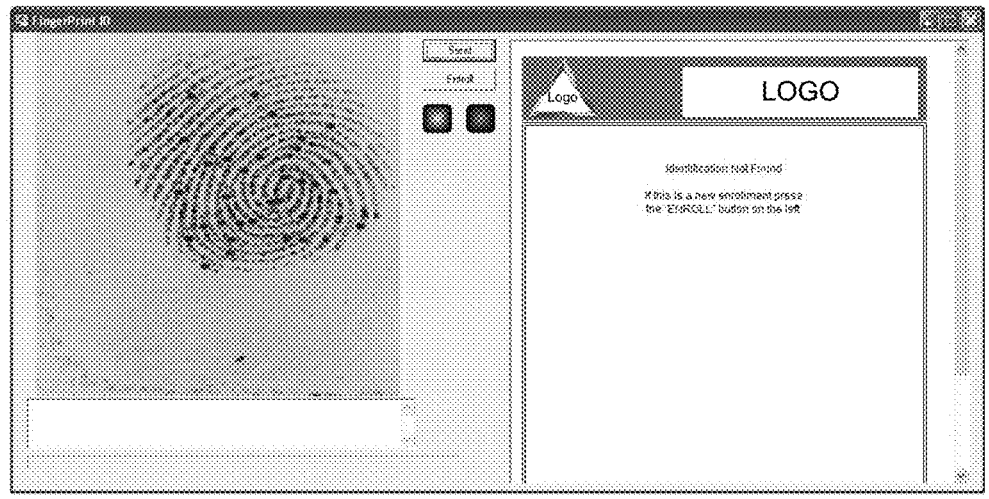
Figure 3F:
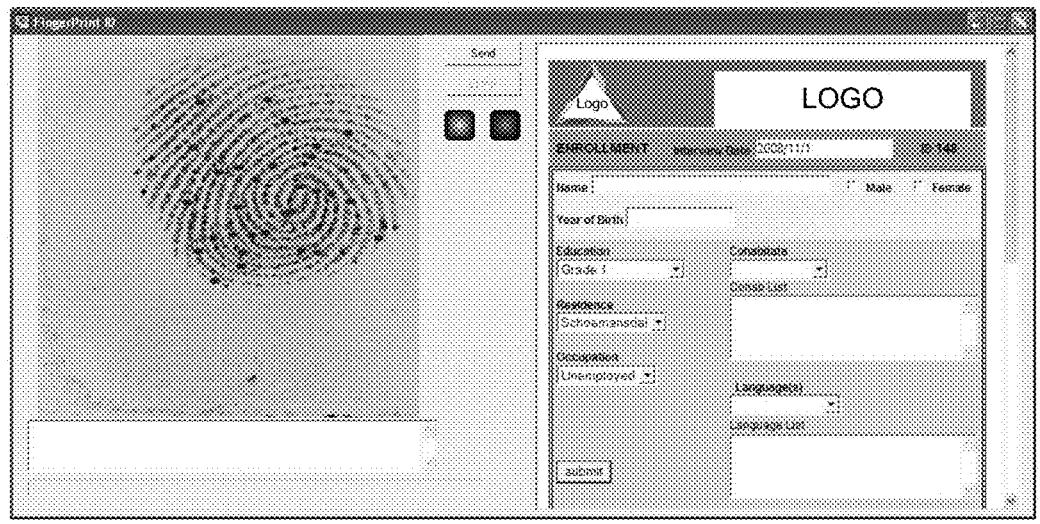
Figure 3G:
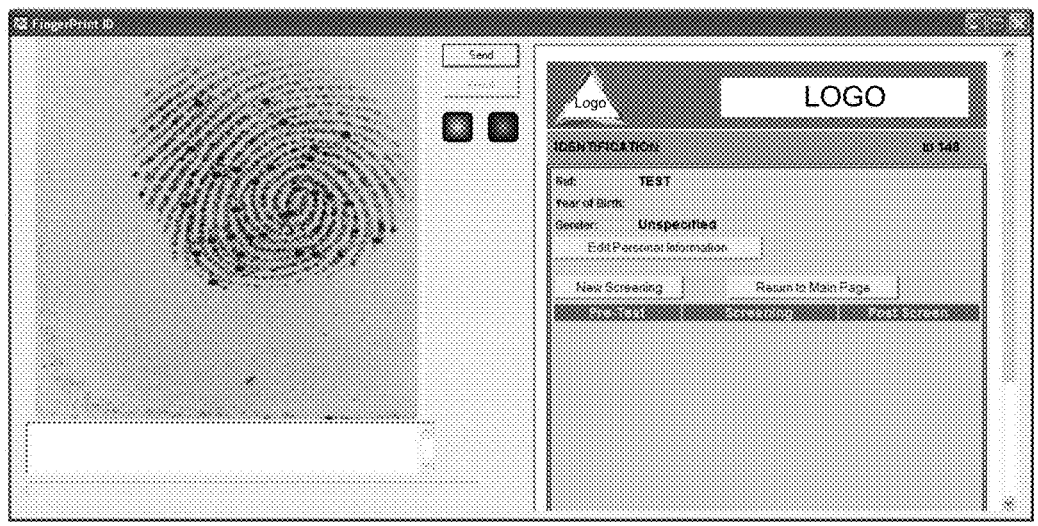
Figures 3H, 3I:
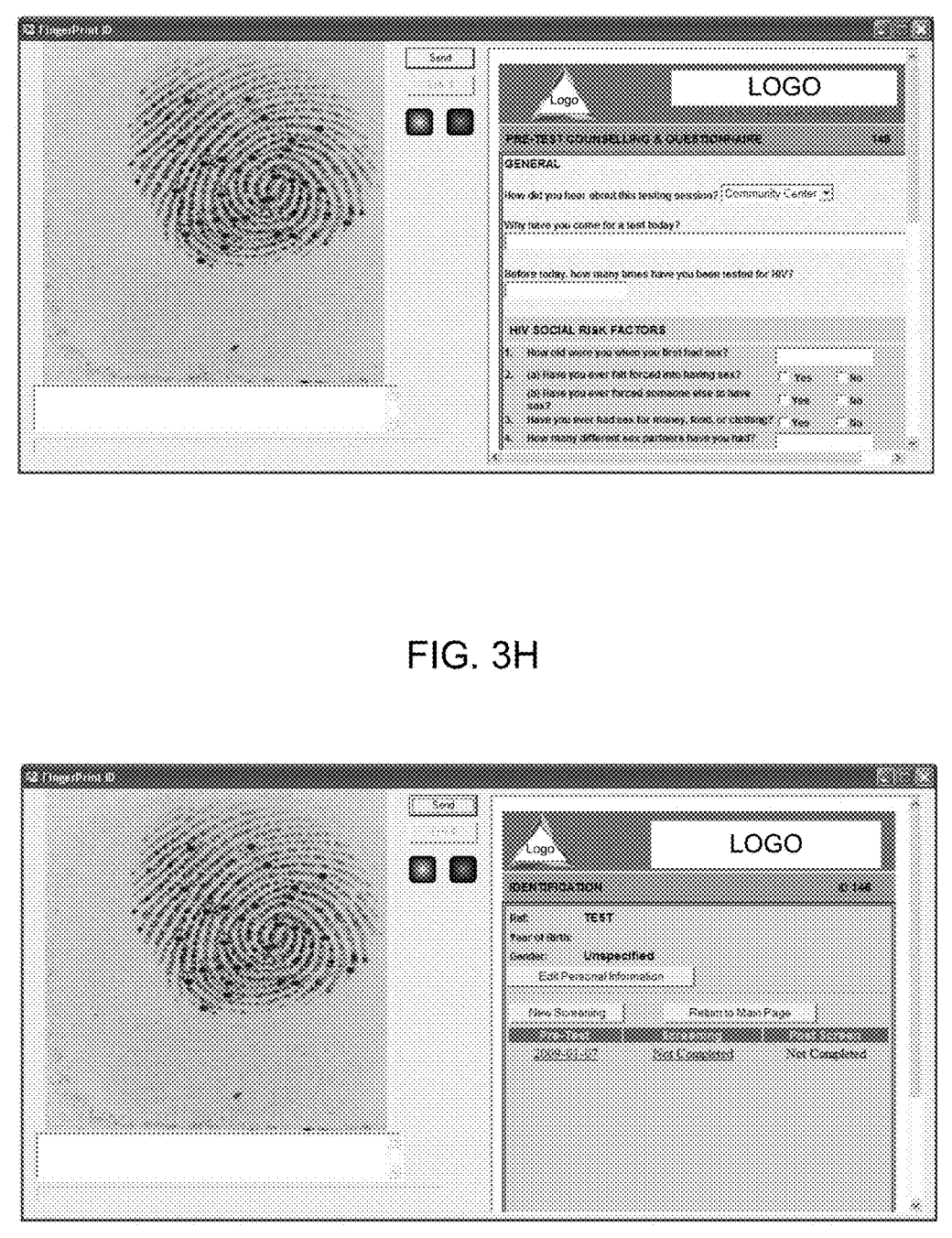
Figure 3J:
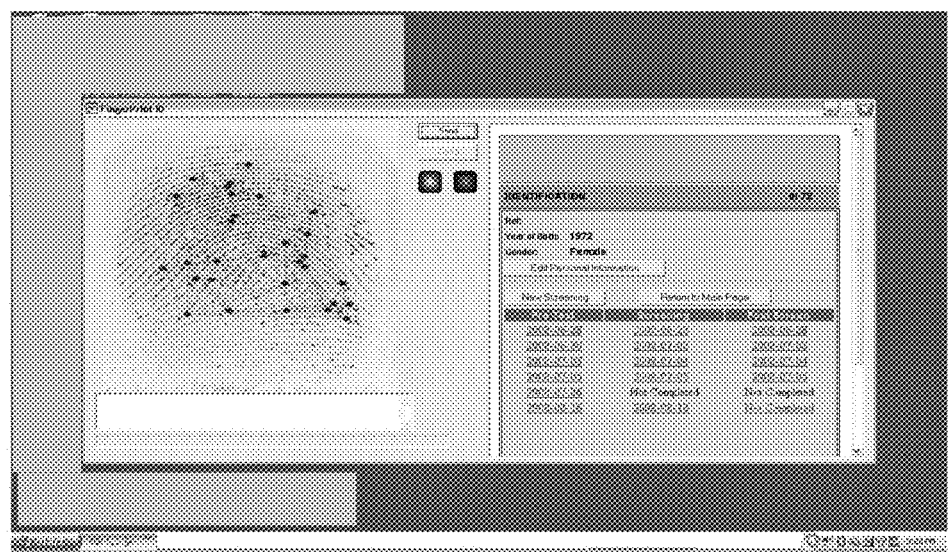

Referring to FIG. 3J, in one embodiment, if the fingerprint data is found in the database, the individual's prior record(s) are retrieved and displayed. In one embodiment, the user transmits biometric data via a URL to a remote server. In turn, the remote server retrieves and displays client/patient records. In one embodiment, no name, SS#, or other client identifier is displayed because no personal identifiers other than gender and year of birth (YOB) are taken.

As shown in FIG. 3E, in one embodiment, if the fingerprint data is not found in the database, the RemoteID application returns a message and allows the user to add (enroll) the new individual's fingerprint (scanned template) to the database. The template does not include an image of the fingerprint in one embodiment.

Referring to FIG. 3F, in one embodiment, an exemplary first screen in the enrollment process is shown. The enrollment process creates an entry in the database for the new individual. Demographic data is requested and associated with the fingerprint data. This becomes the main entry in the database for this individual.

Referring to FIG. 3G, in one embodiment, once the new individual's data is submitted, the user is offered additional data management options to add (in this embodiment) a new HIV screening session and to edit the demographic data. This page can also be displayed when an existing fingerprint is identified. Any previous HIV screening sessions (or other data records) are displayed and the user can review existing data or begin a new screening session.

In this exemplary embodiment of the disclosure, each screening session is divided into three sections and is typically completed in order; the pre-screening questionnaire, the HIV screening and the post-screening questionnaire. An exemplary data acquisition form, a pre-screening questionnaire page, is shown in FIG. 3H.

Once each session (data collection) segment is completed it is time stamped and committed to the database. The user progresses in the pre-test, screening, post screening order as shown below. As shown in FIG. 3I, the individual has completed the pre-test questionnaire, but not the screening or post-test screening.

In one embodiment, the only way to view data for a particular individual is for that individual to have his fingerprint scanned and sent to the server. As shown in FIG. 3J, if the server finds the scanned template, various types of information are delivered to a computer or the workstation. In one embodiment, after a successful query and the identification of an enrolled member of a population of interest, a graphic user interface page is displayed. In one embodiment, the interface is an "Information" page. That page or user interface screen contains information on each prior session where all previously completed forms can be reviewed. Since names are not typically retained (although they could be using the Name field in the form) there is no absolute way to access a particular individual's data except by fingerprint. There is, however, a method to access ad-hoc individual information based on the unique ID value (record #) that is issued to each individual. When the reporting is completed, useful aggregated data can be retrieved directly from the database by an authorized user using Microsoft Access or other ODBC compliant database application.

Figure 4A:
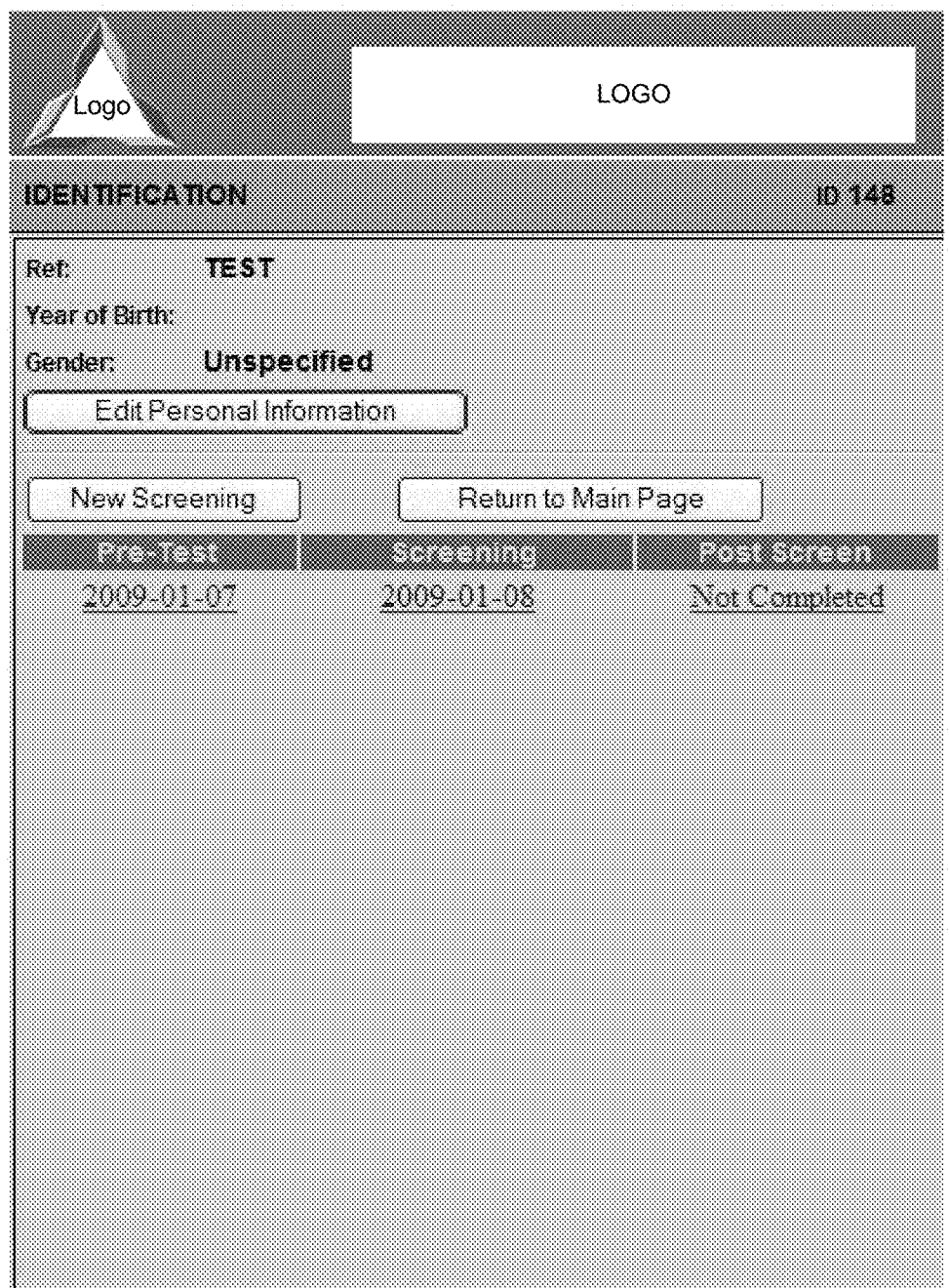

When a fingerprint (or other biometric identifier) is scanned, sent to the server and recognized, the user arrives at the "Identification" page, as shown in FIG. 4A, showing previous data acquisition sessions and dates, in accordance with one embodiment. This page also allows for creating a new session. Clicking on any date link retrieves the previously stored data. A newly enrolled fingerprint (scanned template) will have no dated entries (no data acquisition sessions).

Figure 4C:
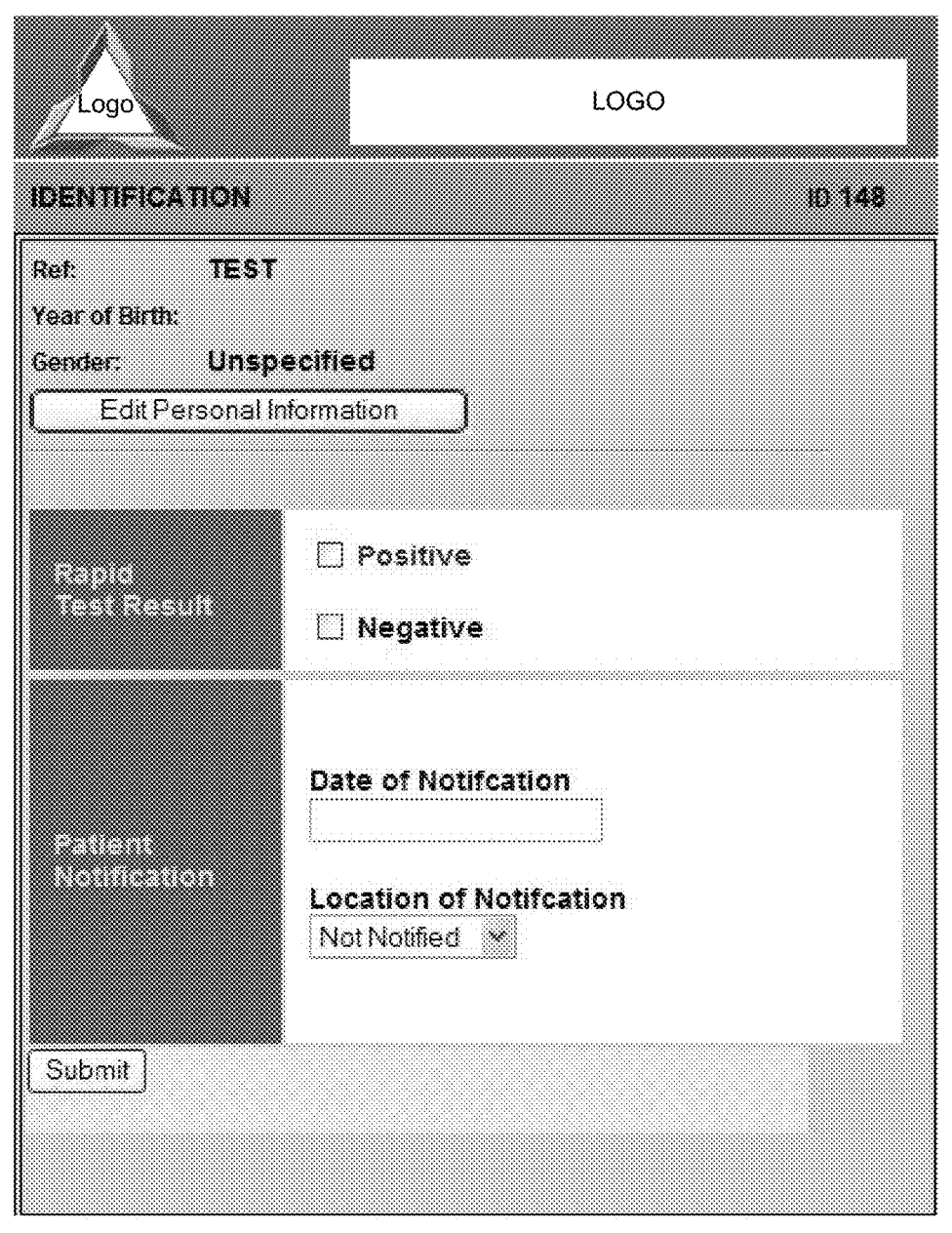

Creating a new data acquisition session requires entering data into each form in this exemplary embodiment in a pre-set order (pre-screening questionnaire, screening and post-screening questionnaire). FIG. 4B shows an exemplary pre-test counseling and questionnaire form. FIG. 4C shows an exemplary identification screening form. FIG. 4D shows an exemplary post-test questionnaire, which can include questions about the individual's medical history. In other embodiments the sequence of forms completion may be customized to be any in any suitable order that varies from application to application.

Specific Non-Limited Uses and Examples

The method, device, and system embodiments described herein facilitate the collection of personal data from members of a population of interest at remote locations such that the personal data can be stored at one or more locations while maintaining the anonymity of the individual members of the population that contribute to the overall data regarding the population.

In light of these features, the embodiments described herein can be extended to various fields of interest. Specifically, the personal data collection and confidentiality maintain features of the present disclosure are amenable to use in all of the following:

Healthcare management
Homeland Security
Double-blind research projects
Pharmaceutical trials,
Marketing & product preference trials
Census data collection
Research on drug addict populations
Follow-up care for health care independent of location of delivery
Remote field research
Crisis & emergency record management
Parole/probation management system
Event or program participation/attendance management
Standardized testing data collection
and various other fields and disciplines in which remote data acquisition and confidentiality and/or anonymity are potential concerns or requirements Report Example I

| male | female | Residence | People in Household | Education | Languages Spoken | Occupation | YOB |
|---|---|---|---|---|---|---|---|
|  | 1 | Village A | Mother/Sister/Brother | Grade 1 | Siswati | Unemployed | 1981 |
|  | 1 | Village A | Brother/ | Grade 10 | Siswati/English | Student | 1982 |
|  | 1 | Village A | Grandmother/Brother | Grade 12 | English/Xitsonga | Unemployed | 1983 |
|  | 1 | Village A | Father | Grade 12 | Siswati/English | Unemployed | 1981 |
| 1 |  | Village B | Mother | Grade 6 | Siswati/ | Unemployed | 1981 |
|  | 1 | Village A | Grandfather/Husband | Grade 1 | Xitsonga | Unemployed | 1981 |
|  | 1 | Village A | Husband/Son/Daughter | Grade 1 | Xitsonga | Unemployed | 1987 |
|  | 1 | Village A | Son/Daughter | Grade 1 | Xitsonga | Unemployed | 1983 |
|  | 1 | Village A | Brother/Son | Grade 1 | Xitsonga | Unemployed | 1981 |
| 1 |  | Village C | Wife/Son/Daughter | Grade 11 | Siswati | Unemployed | 1981 |
|  | 1 | Village C | Son/Daughter | Grade 1 | Xitsonga | Unemployed | 1981 |
|  | 1 | Village A | Husband | Grade 1 | Siswati | Unemployed | 1987 |
|  | 1 | Village C | Husband | Grade 1 | Siswati | Unemployed | 1981 |
| 1 |  | Village A | Mother/Sister/Brother | Grade 11 | Siswati |  Student | 1984 |

One embodiment of the disclosure relates to methods and systems for using secure biometric parameters to remotely access electronic databases while rendering the underlying user data, such as patient data, anonymous. Thus, a member of a population, such as person suffering with a disease or infection, can anonymously enroll for treatment or research using a biometric identifier as the sole method of tracking such an anonymous member of a population of interest. The actual research data collected, albeit anonymously, can be acquired at remote locations where the disease is spreading and analyzed at a facility remote from the population of interest. In part, one embodiment of the disclosure relates to a biometrically secure method of accessing a remote electronic database transmits electronic records using unique biometric features to ensure security.

One embodiment of the disclosure relates to methods and systems for using secure biometric parameters to remotely access electronic databases while rendering the underlying user data, such as patient data, anonymous. Thus, a member of a population, such as person suffering with a disease or infection, can anonymously enroll for treatment or research using a biometric identifier as the sole method of tracking such an anonymous member of a population of interest. The actual research data collected, albeit anonymously, can be acquired at remote locations where the disease is spreading and analyzed at a facility remote from the population of interest. In part, one embodiment of the disclosure relates to a biometrically secure method of accessing a remote electronic database transmits electronic records using unique biometric features to ensure security.

Emergency and Medical Data Related Embodiments

Figure 5:
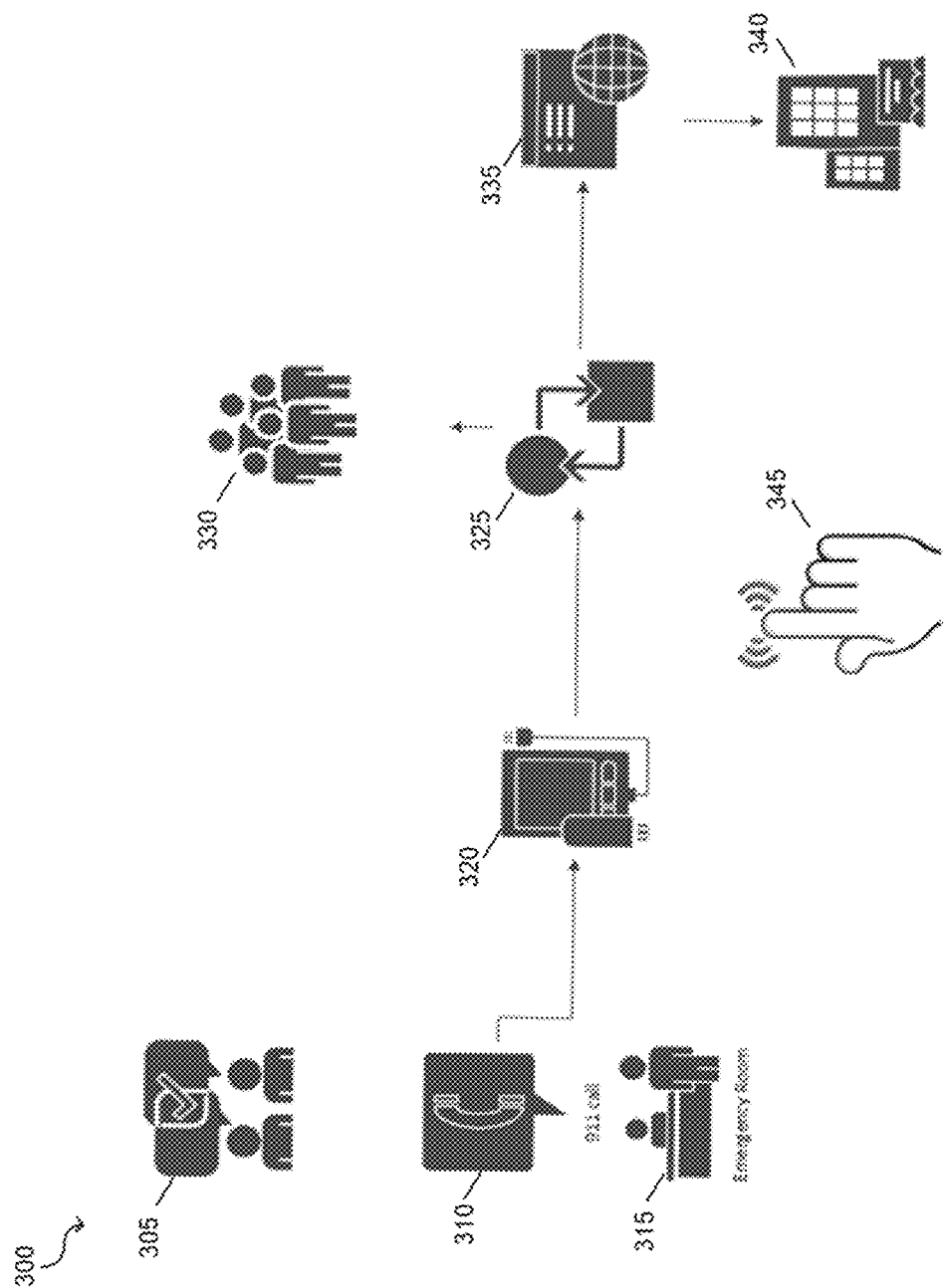
FIG. 5 is a schematic diagram depicting an emergency medical record retrieval and communication system according to an embodiment of the disclosure.

FIG. 5 is schematic diagram depicting an emergency medical record retrieval and communication system 300. As an example, as otherwise described herein the system can be used if a user was in a terrible car accident. If the user suffered a head injury and is stunned, by the time the paramedics arrive, the user is unconscious. The user can't tell them that he is on a blood thinner. As first responders transport the user to the nearest hospital, they call ahead to tell the ER when you'll be arriving. They know the user's vitals, but don't know yet that the user is at greater risk of hemorrhaging. Upon arriving at the ER, doctors will first have to do blood work and order a CT scan before they recognize the user's additional risk. Only then can they give the user life-saving fresh frozen plasma to reduce the chances of a brain bleed. Precious time is passing as they await results before sending the user for surgery. The systems and methods described herein address these and other user incidents.

Now imagine that as soon as the first responders show up on scene, they scan the user's finger using a mobile device or other computer running an embodiment of the emergency record retrieval and communication software. Within a few seconds they know exactly who the user is, what meds are in the user's body, the user's allergies, and the user's acute history. Immediately upon arriving at the hospital, the ER team treats the user with the plasma A user need in preparation for life-saving surgery. In one embodiment, subject to the options and preferences a user selects via a user interface screen in the software, one or more of the user's family, primary care physician, and insurance provider are notified about what's happening. By enrolling at the doctor's office, a hospital, a kiosk, or with a mobile device by themselves or another scanpoint, the embodiments of the disclosure avoid these and other dangerous scenarios.

The disclosure includes a real-time mobile service that enables those first responders and emergency medical personnel to access essential information using only a patient's fingerprints to retrieve it. Annual subscribers to the service choose which information to make available in this private, HIPAA-exempt registry. In one embodiment, the information stored by a user and indexed using a template or identifier generated in response to a scan of a finger or other user feature is not an electronic health record. Instead, in one embodiment, the stored information is a private biometrically-secure vital health registry. Only authorized medical and emergency personnel have the application on their mobile devices to access the user's information. The first responders and other personnel are authorized to view the records as a result of the voluntary enrollment of the user.

Emergency Medical Service Agencies around the country respond to more than 50 million calls each year. Add to that another 130 million ER visits. Factor in nearly 50% of children with autism who wander from home, and that more than 60% of people living with Alzheimer's will wander more than six times before moving to a residential facility. There is a compelling need for first responders and emergency medical personnel to access individuals' essential health information instantly and securely.

With the Affordable Care Act incentivizing reduction in costs, adverse events, and errors, every health care system and payor is seeking ways to mitigate costs and risks related to emergency medical treatment. Hundreds of millions of dollars in Emergency Department-related medical malpractice claims are awarded each year. Billions more are spent by physicians, hospitals, and health and life insurance companies to manage patients' care for these adverse events and errors.

The embodiments of the disclosure can be implemented using various data and information processing platforms such as Microsoft's HealthVault platform. The implementations can be configured to ensure the highest level of security for the personal and health information that they want to share in a crisis.

The embodiments can be used by primary care physician networks and school district networks to provide the benefits to the foregoing and subscribers. By offering instant incident linkage to health insurance companies and more robust services to subscribers than existing resources, the system can enroll more than millions of subscribers. First, subscribers may pay an annual fee. Partners in the private health payor space pay per subscriber for instant reporting linkage when a subscriber is transported or admitted to an ER. Other payment options can be implemented as desirable.

Patients in emergency situations often have no way of communicating life-saving information to first responders (firefighter/EMTs) and emergency medical personnel (ER doctors and nurses). That lack of information leads to treatment errors, loss of life, and billions of dollars in avoidable care costs for patients, EMS agencies, doctors, hospitals, and insurance companies.

The emergency data retrieval and communication software and related systems and methods provide a real-time service that will enable first responders and emergency medical personnel to access patients' vital health information simply by scanning the subscriber's fingerprint into an app on the first responder's or provider's internet-enabled mobile device or desktop system. Subscribers choose what information to share: allergies, current medications, prior surgeries and other information of interest. This information is automatically linked with an RX database such as a central national electronic prescription database. The Rx database is accessed using an interface in the software as a pass through to lookup Rx data, at the time of an incident, and retrieve "active" prescriptions and/or historic prescription information. In one embodiment, the user record in the subscriber database will not store any non-self-reported medication information, chronic conditions, and acute health history. This can be overridden by user preferences and consent in one embodiment.

The emergency data retrieval and communication software and related systems and methods also provide real-time incident notification to subscribers' emergency contacts and forwards profiles retrieved on-scene onward to the emergency room or other treating entities. The emergency data retrieval and communication software and related systems and methods also transfer certain fields from a subscriber's profile into the first responders' electronic Patient Care Reporting (ePCR) software (3rd party vendors). Further, the software will also display for users a log of every time the subscriber has been seen by the system (either by EMS or in an Emergency Department in a hospital) as a patient. This will be one way for users to see if a patient might be seeking pain medications or at high risk for certain other conditions.

As shown in FIG. 5, the system 300 includes various stages and method steps. Initially, as a first step there is an enrollment process. As shown in step 305, a subscriber enrolls in the emergency data communication service by having their fingers scanned and enters other relevant personal information. The scanning or registering of a user's fingerprints shown in step 345 occurs at enrollment and also occurs in the event the user requires medical treatment such as during an incident and is then scanned to obtain their records.

In one embodiment, subscribers enroll by creating a profile via a web-based link to the provider of the service and initiates the enrollment process, or at an actual ScanPoint kiosk doing the same thing—to be described below). The subscriber will enter information such as name, insurance policy info, emergency contacts and their phone numbers, code status (Do Not Intubate, etc.) acute history, chronic conditions, allergies, address, and special instructions. As an example, the special instructions such as for kids with autism who might not like to be touched or need to be spoken to in a quiet voice, this can be noted in their retrievable record. The subscriber or his proxy (parent/guardian) will also set access permissions for different kinds of responders (he can choose to allow hospital-based care providers to retrieve information, but maybe he doesn't want EMTs to have access).

In one embodiment, the system and methods described herein enable users, such as subscribers to a service, to upload their own copies of certain documents, such as EKG, chest xray, and living will. In one embodiment, the systems and software disclosed herein do not store such records on its servers and as part of its databases but instead retrieve them from a third party storage provider during an incident.

If the subscriber is enrolling at home/office/not at a ScanPoint, at the end of the enrollment process, the subscriber will be prompted to enter his ZIP code in one embodiment. The system will index and store all of the ScanPoints and address/ZIP. In one embodiment, the interface screen will then display the nearest 5 or 10 ScanPoints (often fire departments, hospital emergency rooms, retail pharmacy, kiosks, doctor's offices, residential homes for senior citizens, school nurse offices, etc.). The system also includes various mobile enrollment systems set up on laptops/tablets for certain community health employees to use at events where people can enroll, etc).

The subscriber will go to a ScanPoint and create an identifier that will be linked to their record based on their fingerprint scan. That identifier will populate a field in the subscriber's profile in the database and be the primary retrieval key during an incident query.

When the subscriber is at a ScanPoint, he will click on our app (if it is not a dedicated kiosk). Next, the user will be prompted to enter the username/password he created during the profile creation portion of the enrollment process. If no profile is recognized, the subscriber will be prompted to create one and fill out all the above-listed info. If the profile is recognized, the subscriber will be prompted to register each and every finger (scanning each finger a few times to create a good template). The system will confirm that each finger is registered. When all fingers are registered, the subscriber's profile is complete and in theory, should be "ready" to be read by a care provider in an emergency.

Figure 6:
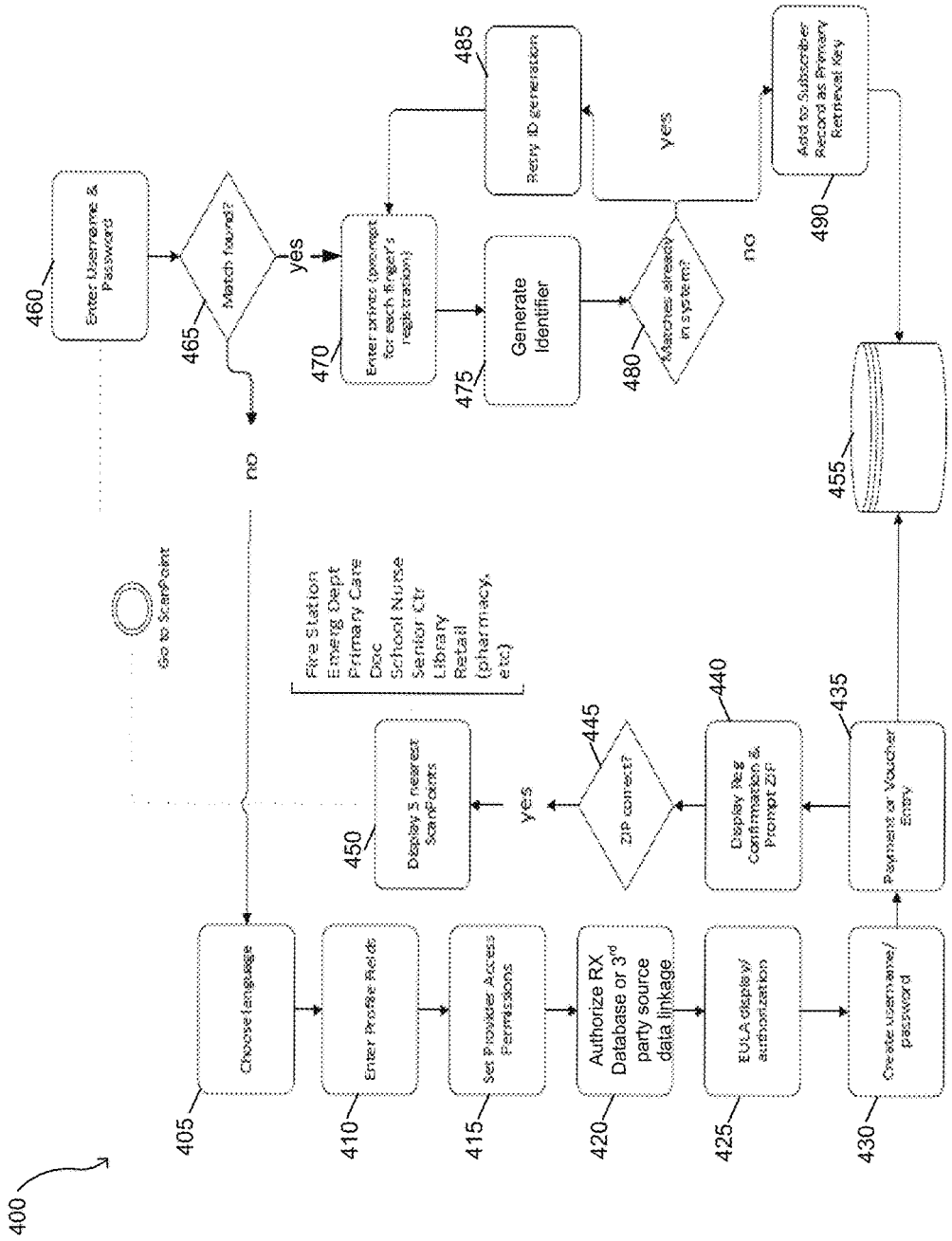
FIG. 6 is a schematic diagram depicting an exemplary enrollment process flow an emergency medical record retrieval and communication system according to an embodiment of the disclosure.

The subscriber will also grant permission for the emergency data retrieval and communication software to ping the Rx Database to retrieve current medications during a medical emergency. The subscriber will create a username and password so he can later retrieve his profile when registering his fingerprints/creating a template-based identifier for his records and for when he wants to update parts of his profile from home. Billing information may be collected at this point. Billing info can either be paid directly by subscriber or (still designing this) via a "voucher" issued by an insurance company/benefits provider. FIG. 6 shows a flow chart that depicts various steps of a method of the disclosure relating to enrollment and identifier registration in further detail.

Returning to FIG. 5, after enrollment the user's record and preference are active in the system. In the event there is an emergency involving a user, an emergency call is initiated step 310. This call will also initiate action at the emergency room step 315. When a first responder or emergency room personnel is with the user, they scan the finger using a device in communication with a processor and memory storage that is running the communication and retrieval software or app step 320. In turn, the software contacts a server that includes the relevant databases and searching tools that can process a scanned identifier such as a template. The software retrieves the patient provided history, allergy information, and medical Rx or other information and transmits it to the mobile device or computer of the first responder or ER personnel Step 325.

Figure 7A:
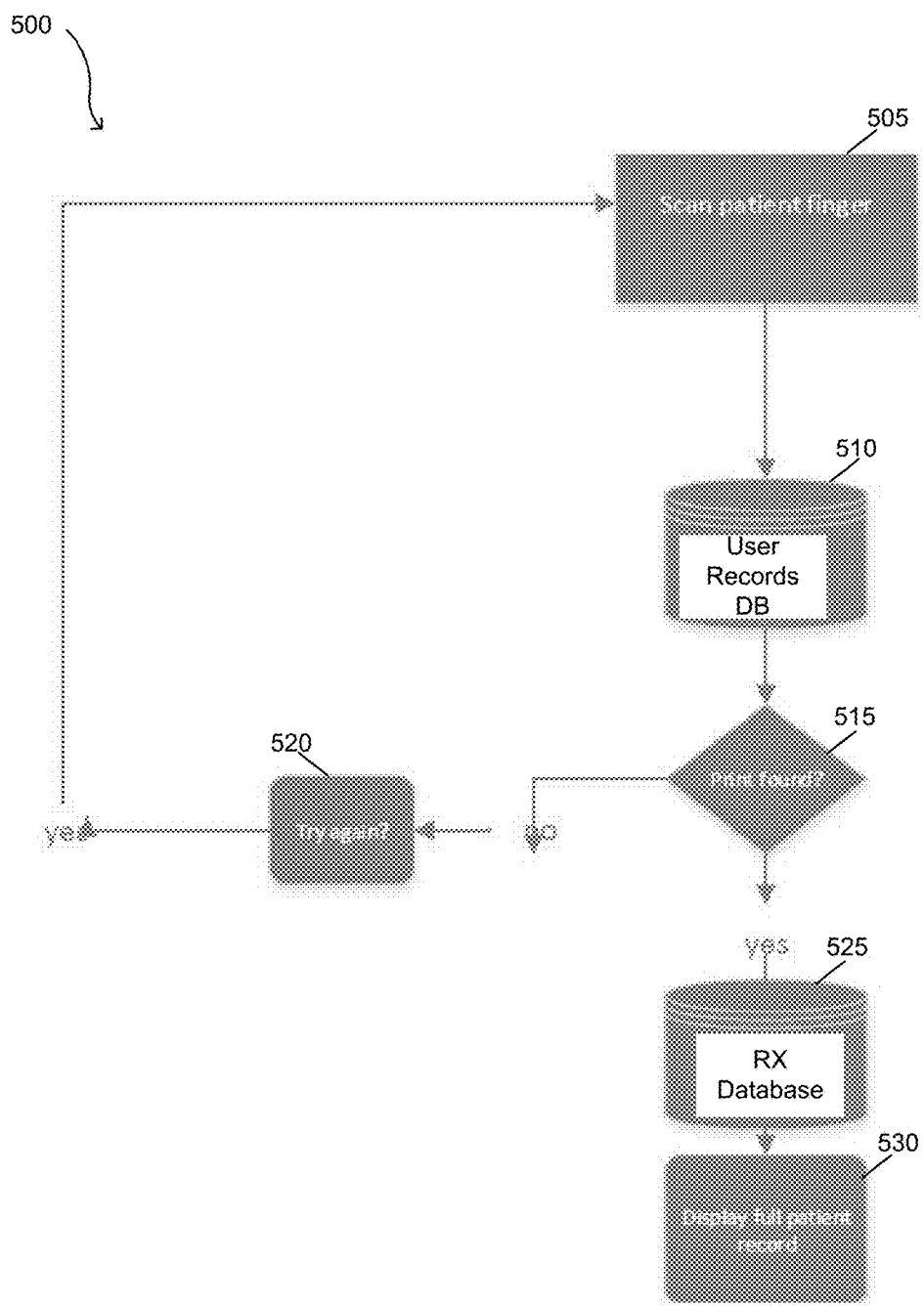
FIGS. 7A and 7B are schematic diagrams depicting an exemplary retrieval process flow for an emergency medical record retrieval and communication system according to an embodiment of the disclosure.
Figure 7B:
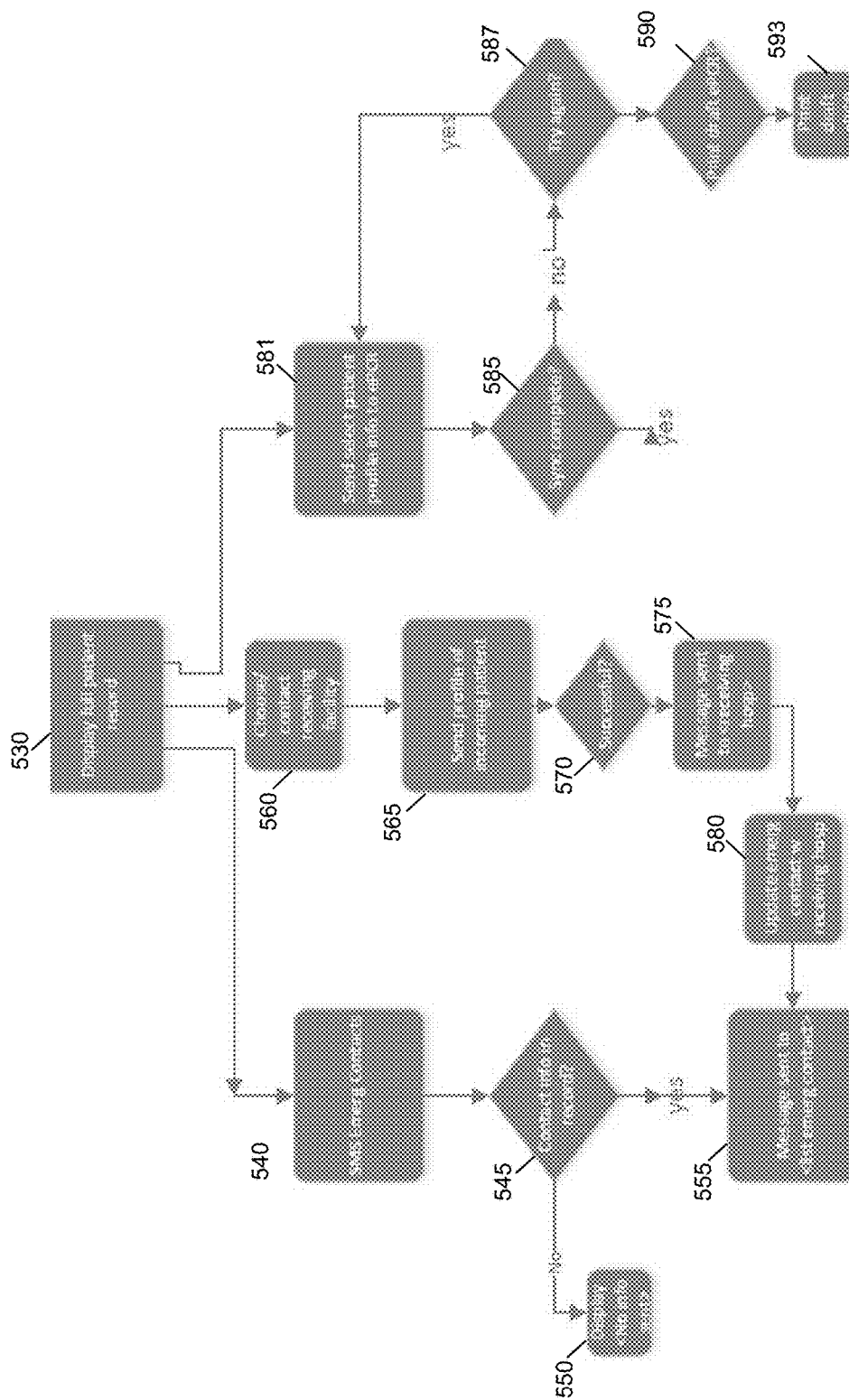

In one embodiment, the software automatically notifies the patient's emergency health contact and primary care physician or case worker step 330. As a result, the first responder or ER personnel can treat the patient with up to date information step 335. The software can also automatically generate and transmit an update with regard to the patient's indexed medical information and deliver that to emergency contacts, insurance provider, and/or primary physician step 340. FIG. 7A which is continued in FIG. 7B includes a process flow that identifies some exemplary steps that can be triggered in response to scanning a patient's finger that is enrolled in the system.

An incident begins either in a hospital emergency department with an authorized member of the hospital team or on scene with an authorized first responder (EMS, firefighter, etc). The authorized user will open the emergency data retrieval and communication software or app, scan the patient's finger. If the patient is a subscriber, the emergency data retrieval and communication software and related systems and methods will retrieve and display the profile—which will include the self-reported information and any current medications retrieved from the Rx Database system. The software will also display the subscriber's "hits" to the system within the past X days, such as 10, 30, 90, or some other number of days on a user interface. The healthcare provider will consult this information during the course of treatment/transport. The user will also be able to send an alert to the subscriber's emergency contacts by clicking on the button beneath those contacts. One or more of servers that constitute part of the system that interfaces with the mobile device or computer-based software will send an automated SMS/email (depending on type of contact info subscriber provides for each contact).

If the patient is initially being treated by an EMT/Paramedic outside of a hospital setting and is transported to a hospital, the first responder can send a snapshot of this patient info ahead to the receiving hospital ER (how that info is received and displayed can be specified using an interface pursuant to user preferences). This ER alert will also update the emergency contact, letting the contacts know that the patient is being transported to the specific hospital. Upon arrival at the hospital, the triage nurse or other authorized receiving emergency department personnel will scan a patient's finger to confirm the correct patient info/ensure proper continuity of care.

One or more software application embodiments will respond to inputs from a first responder user (and possibly for hospital emergency departments, as well) to perform data transfers of certain pre-determined fields to populate corresponding fields in the ePCR system or hospital patient registration system. In one embodiment, system uses an application programming interface to communicate data with one or more ePCR vendors.

Figure 8:
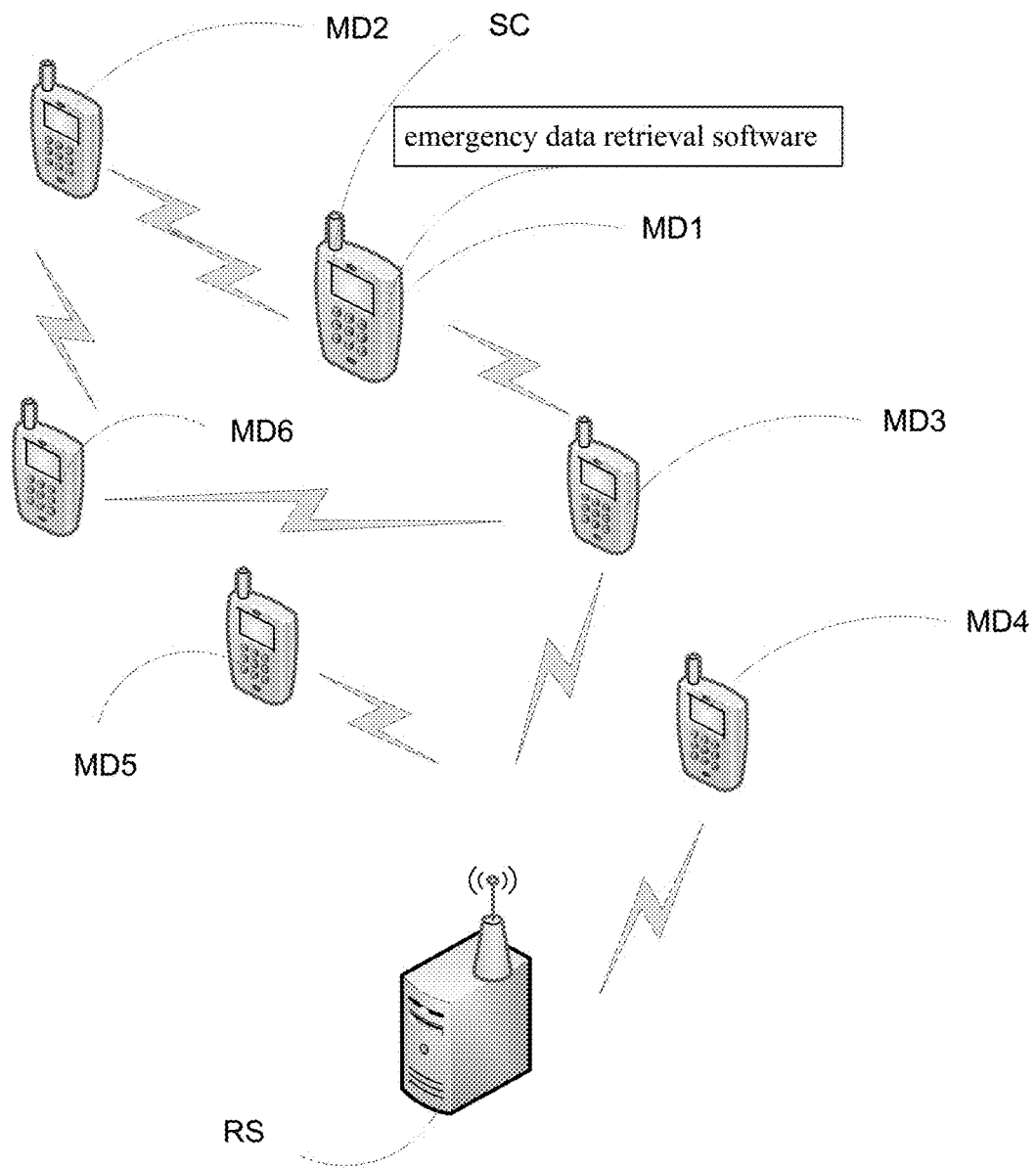
FIG. 8 is a schematic diagram depicting an exemplary network configuration with direct mobile device communications during a phone or internet outage according to an embodiment of the disclosure.

FIG. 8 shows a plurality of mobile devices MD1-MD6 in communication with each other. A record server RS is also shown which can communicate with the mobile devices. Each of the mobile devices includes a SIM card SC. The arrangement of mobile devices shown in figure illustrates a feature of the disclosure that is relevant in the event communication service outages. For example, in the event there is a catastrophe such as an earthquake or MCI as a result of running the software on each mobile device each device acts as a node in a network by which other devices can communicate and exchange data. Thus, the arrangement shown in FIG. 8 represents an interconnected network of individual mobile devices that can communicate and exchange data relating to patient records and in the event of a loss cellular network communications. In one embodiment, the SIM card of each mobile device has the application software permanently or persistently installed thereon such that the ability to access patient information is available during a service outage. In addition, in one embodiment, the SIM card can also have a version of the patient's records database stored thereon.

As shown in FIG. 8, the mobile device includes a SIM cards or other persistent memory such as an EPROM or other memory element that is not erased during a reboot or reset process. In one embodiment, the medical information retrieval application and one or more of identifier generation, identifier verification, identification protocols, and direct signaling and communication protocols for a mobile device are stored on the SIM card or one of the aforementioned memory elements. In one embodiment, the mobile device includes protocols to permit communications using Unstructured Supplementary Services Data or USSD and to communicate using a USSD gateway or center.

There are tradeoffs between functionality and security when it comes to porting subsets of the subscriber database onto a local machine. In one embodiment, based upon a predetermined schedule, for example, every morning, the system and one or more software components executes an update routine to download a secure file containing one or more profiles of subscribers to a local device. In one embodiment, the profiles are selected in response to the subscribers who list their home zip code within the catchment area of the EMS agency. As a result, a local regional copy of the relevant medical records can be downloaded to hedge against outages or loss of network connectivity. In the event of a local or regional accident, such as a blackout and accidents, such an implementation has numerous advantages.

The system and related methods are optimized for a fully online context, but it is possible to configure medical personnel's devices running the emergency response software to work in a streamlined, offline context. Instead of having search/match process happen at the server level, we enable these local devices to run the entire app and match against a subset of the master subscriber database that contains the most likely population to need system (i.e., only those with the ZIP code within 30 mile radius of service agency). There is some limited functionality in this use case (i.e., no real-time connectivity with Rx Database temporarily suspends ability to ping for up-to-the-minute prescription info; no real-time emergency contact alert & any other functionality that requires internet connectivity).

Figure 9:
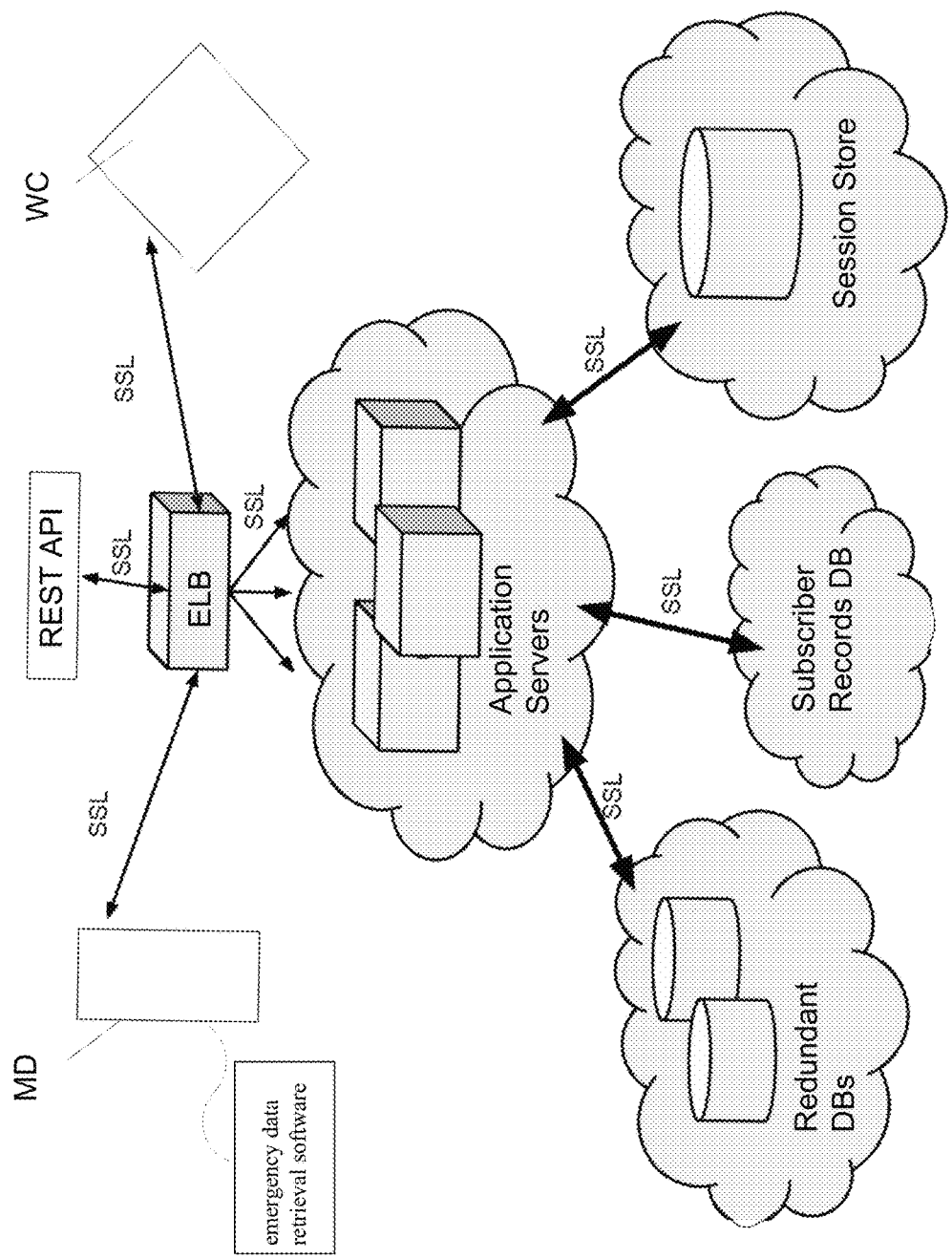
FIG. 9 is a schematic diagram depicting an exemplary network configuration for an emergency medical record retrieval and communication system according to an embodiment of the disclosure.

FIG. 9 is a schematic diagram of various components of a system suitable for implementing the emergency information retrieval and communication features described herein.

The system includes an elastic load balancer or ELB. The ELB is in secure communications with a client WC such as web client. The client WC is used for user onboarding, record management, notifications, and detailed medical record information, as well as administration in one embodiment. The ELB is also in secure communication with one or more mobile devices MD. Each mobile device includes a built in scanner, touch screen controlled to perform fingerprint scanning, or is connected to a scanner. Client software interprets scan and creates encrypted binary data representation of fingerprint image. The client software is also used to quickly deliver medical data to first responders.

In one embodiment, the ELB also connects to a Representational State Transfer (REST) API which includes instructions to integrate with third party platforms such as the RX Database and others. The ELB is also in secure communication with one or more application servers. The application servers are in secure communication with various databases. The application servers are in secure communication with one or more redundant databases. The redundant databases can be implemented using various platforms such as PHP/MySQL or NodeJS/MongoDO.

Figure 10:
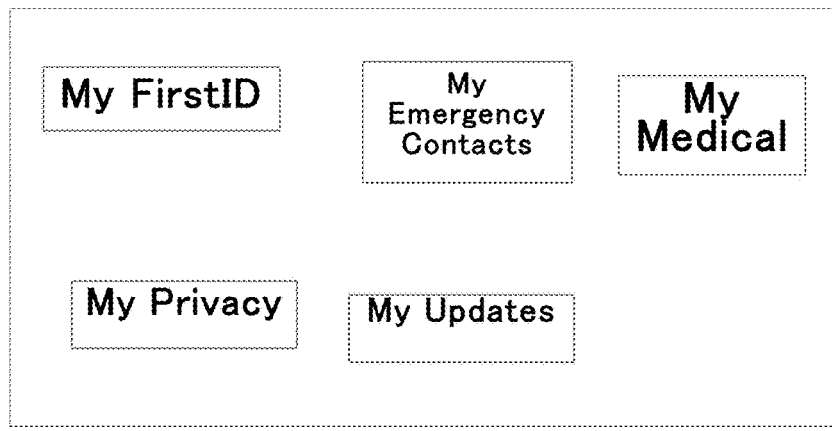
FIG. 10 is schematic diagram depicting an exemplary user interface home screen according to an embodiment of the disclosure.

The system can implement various user interfaces of varying levels including multiple nested levels. A high level user interface is shown in FIG. 10. The various top level interface screens shown include My FirstID, My Emergency Contacts, My Medical, My Privacy and My Updates. These are representative user interface headings. The My First ID interface includes fillable forms and allows a subscriber to update various types of information including First Name, Last Name, Email, Mobile, Date of Birth, Gender, Residential Address, Languages, and Insurance Carrier/Policy.

The My Emergency Contacts interface includes fillable forms and allows a subscriber to update various types of information including Primary Contact: Mobile/Email, Health Care Proxy Contact's Mobile/Email, Primary Physician's Mobile/Email, and Notification types (email/sms/voice). The My Medical interface includes fillable forms and allows a subscriber to update various types of information including Allergies, Daily Medications, and History of Major Health Events. The My Privacy interface includes fillable forms and allows a subscriber to update various types of information including setting access levels that control which individuals or entities can access their profile and the data associated with it and their biometric identifier. For example, the access levels can be set for the following Emergency Medical Technicians & Paramedics, Emergency Dept Hospital Personnel, Pharmacy and Law Enforcement. In addition, the My Updates user interface allows a subscriber to create subscriber profile, create and update password, and set up a security question to retrieve a lost or forgotten password. Additional user interfaces are shown in FIGS. 12E-12F.

The system and methods are designed to comply with various data security and privacy regimes. In one embodiment, multiple levels of encryption are used throughout the process such as SSL, hashing routines, and the creation of a non-image identifier through an application API of the data retrieval software application In one embodiment, the "biometric" identifier generated in response to a fingerprint scan is only partly based on the biometric scan data. In one embodiment, the identifier includes a template which includes the output of the imaging scanning software or a vectorized representation thereof which includes a string of characters. A client code can be added to the template representation to generate a longer string of characters. The client code can be generated based on any number of systematic process across the subscriber set. In addition, in another embodiment an additional universally unique identifier or UUID component (such as MAC address/timestamp at time of first enrollment) is added to the template or the client code plus the template to yield an aggregate user identifier.

Figure 11:
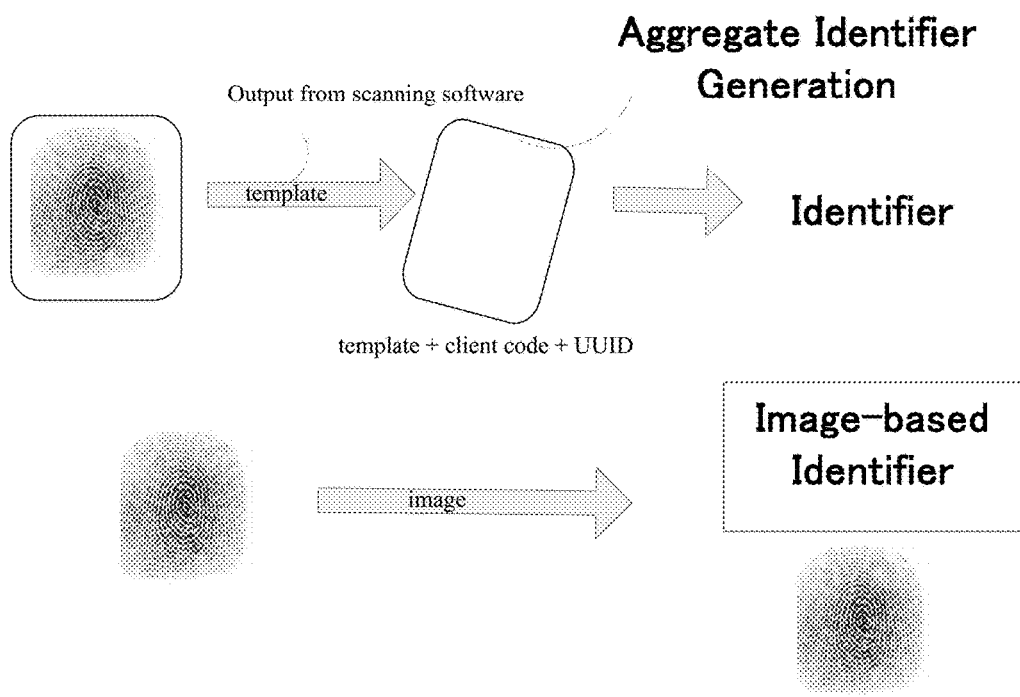
FIG. 11 is a schematic diagram depicting generation of an exemplary aggregate identifier and an image-based identifier an according to an embodiment of the disclosure.

In one embodiment, the aggregate user identifier can include the template, the template+client code, or the template+client code+UUID. An example of an aggregate user identifier being generated is shown in the top portion of FIG. 11, in one embodiment, hashing is applied to the aggregate user identifier or a predicate identifier to create the aggregate identifier. As a result, the hashed aggregate user identifier represents a multi-layered identifier that is user specific but does not include a scanned image of the user's finger print. This offers added security and allows other information to be encoded in the aggregate identifier. In contrast, the bottom portion of FIG. 11 shows an image-based identifier which is less secure and typically avoided in favor of using a template or aggregated code as the identifier.

The system and related methods have a real-time retrieval of current, active medications (and other patient data) as a pass-through in one embodiment. Thus, in one embodiment some data are never resident on our servers/with the subscriber's device. This prevents info overload/dangerous outdated information from reaching care providers (i.e., during an incident, if a patient is recognized by our server as authenticated, our system then accesses the Rx Database and retrieves only "active" prescription. That prescription information is not populated into the subscriber's record in the record database resident on one or more of the system servers. Instead, only a real-time snapshot is generated and shown to the treating medical professional. As noted herein, the report can include other pass through data from other sources such as ePCR data and self-reported data such as allergies, acute history, chronic conditions, special instructions for autism, etc.

Figure 12A:
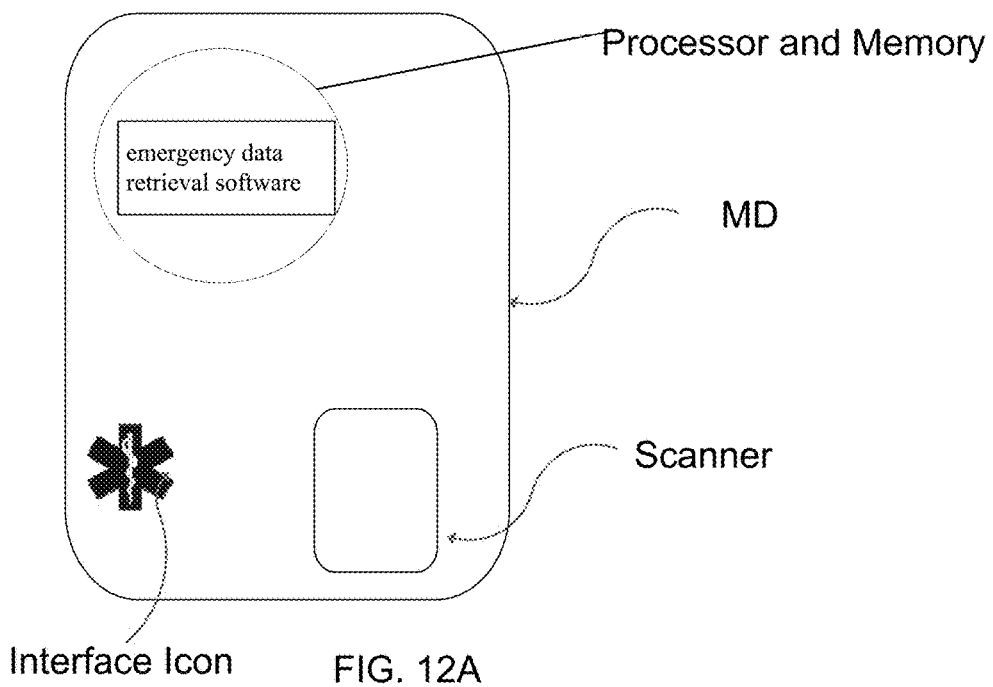
Figure 12B:
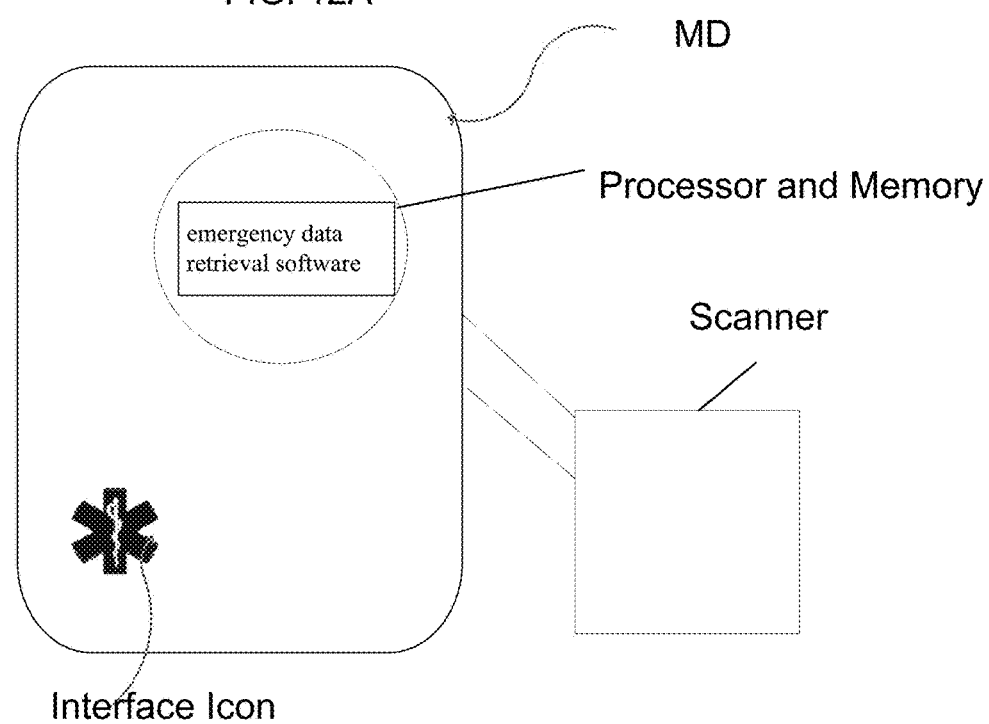
Figure 12C:
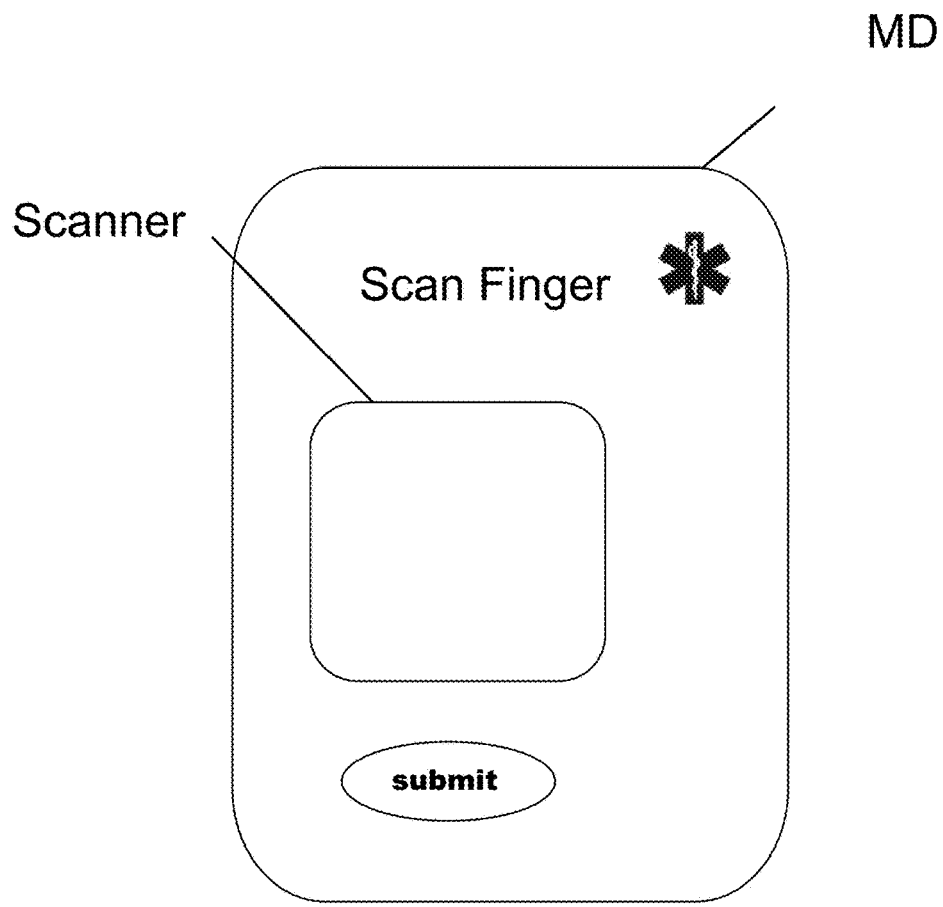

FIG. 12A shows a mobile device MD that is running emergency data retrieval software as an application on the processor of the mobile device. An icon is displayed on the mobile device MD for a user to activate the emergency data retrieval software. This software can be used to enroll and subscriber and to receive medical information by scanning an enrolled subscriber. The mobile device shown in FIG. 12B is substantially the same except that the scanner in FIG. 12A is built into the mobile device such as via its touch screen while the mobile device in FIG. 12B has a detached scanner. In FIG. 12C, a user interface screen showing a region of the scanner to touch a finger for scanning and a submit button to generate the scanned image data is shown.

Figure 12D:
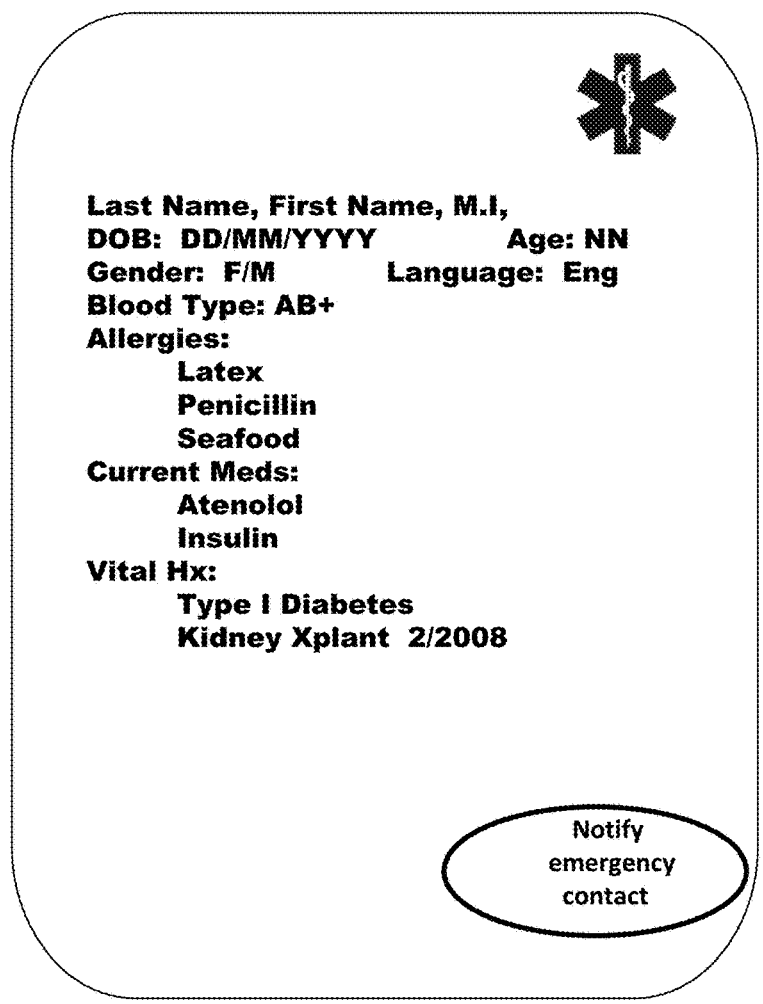
Figure 12E:
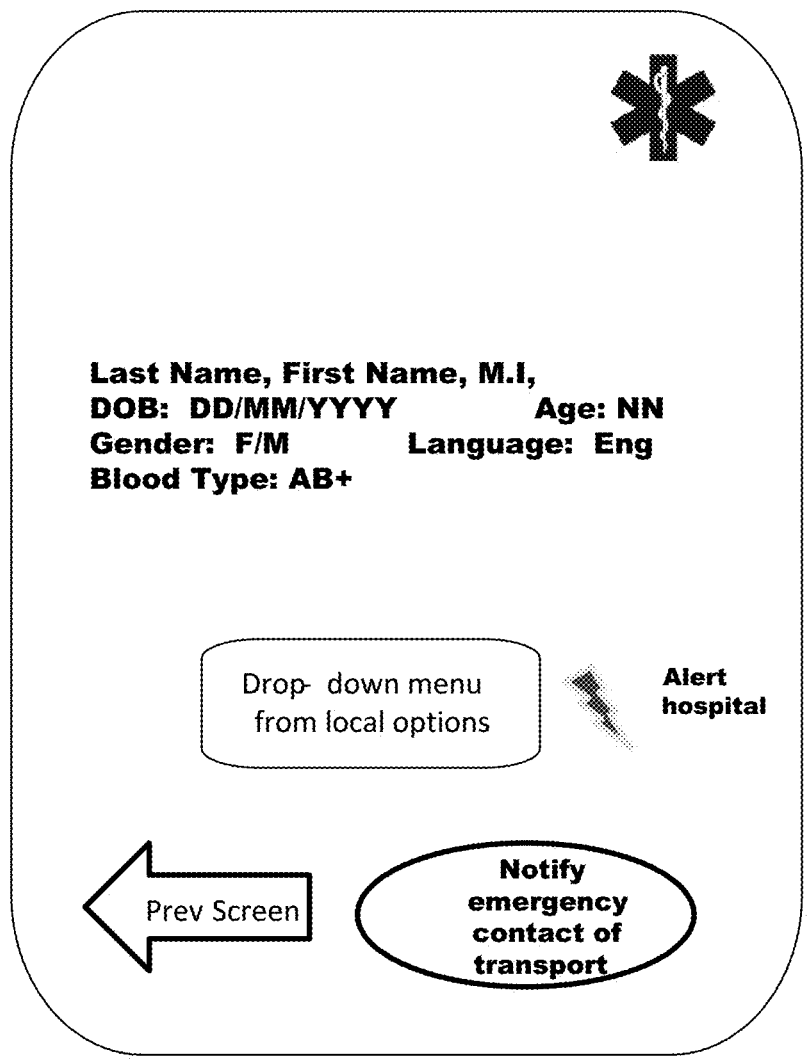

Once the image scan is generated the software application will convert it into a template or aggregate identifier. FIG. 12D shows a user interface screen that includes medical information retrieved in response to a scan of a fingerprint. FIG. 12E shows a user interface screen that includes information notifying the emergency contact that the subscriber is being transported. The hospital is also notified. The subscriber and a summary of their information are included in the middle upper region of the interface screen. FIG. 12F shows another exemplary user interface screen with subscriber medical information.

Non-Limiting Software Features and Embodiments for Implementing Anonymous Biometric Identifier User Data Collection Some aspects of the functional modules described in this disclosure may be implemented, for example, using a machine-readable medium or article which may store an instruction or a set of instructions that, if executed by a machine, may cause the machine to perform a method and/or operations in accordance with the aspects. Such a machine may include, for example, any suitable processing platform, computing platform, computing device, processing device, computing system, processing system, computer, processor, or the like, and may be implemented using any suitable combination of hardware and/or software.

The machine-readable medium or article may include, for example, any suitable type of memory, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, universal serial bus (USB) flash drive, various types of Digital Versatile Disk (DVD), a tape, a cassette, or the like. The instructions may include any suitable type of code, such as source code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, arrangement language, machine code, and so forth.

While various details have been set forth in the foregoing description, it will be appreciated that the various aspects of the data collection and retrieval may be practiced without these specific details. For example, for conciseness and clarity selected aspects have been shown in block diagram form rather than in detail. Some portions of the detailed descriptions provided herein may be presented in terms of instructions that operate on data that is stored in a computer memory. Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities.

Unless specifically stated otherwise as apparent from the foregoing discussion, it is appreciated that, throughout the foregoing description, discussions using terms such as "processing" or "networking or "routing" or "computing" or "authenticating" or "retrieving" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other.

It should be understood that the order of the steps of the methods of the disclosure is immaterial so long as the disclosure remains operable. Moreover, two or more steps may be conducted simultaneously or in a different order than recited herein unless otherwise specified.

The use of sections or headings in the application is not meant to limit the disclosure; each section and heading can apply to any aspect, embodiment, or feature of the disclosure.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

In the application, where an element or component is said to be included in and/or selected from a list of recited elements or components, it should be understood that the element or component can be any one of the recited elements or components, or can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes," "including," "have," "has," or "having" should be generally understood as open-ended and non-limiting unless specifically stated otherwise.

The terms "a," "an," and "the" mean "one or more," unless expressly specified otherwise.

The foregoing, and other features and advantages of the disclosure, as well as the disclosure itself, will be more fully understood from the description, drawings, and claims.

While certain features of the aspects have been illustrated as described herein, many modifications, substitutions, changes and equivalents will now occur to those skilled in the art. It is therefore to be understood that the appended claims are intended to cover all such modifications and changes as fall within the true spirit of the aspects.

I claim:

1. A method of securely retrieving remotely stored data for an individual requiring medical attention comprising:
   enrolling a subscriber in an emergency data retrieval and communication system;

storing medical information for the subscriber in a data storage device at one or more remote locations;

storing a biometric identifier for the subscriber at one or more remote locations;

storing (i) the biometric identifier and the medical information or (ii) a first software application in a persistent electronic memory device of a first mobile device, wherein (i) the biometric identifier and the medical information or (ii) the first software application are only accessed upon occurrence of a network outage that interferes with retrieval of the medical information;

correlating the biometric identifier and the medical information on a per subscriber basis;

retrieving the medical information using the first mobile device in response to input a scan of the subscriber using the first software application running on the first mobile device; and displaying the retrieved medical information on the first mobile device.

2. The method of claim 1 further comprising the step of contacting emergency contact of subscriber when subscriber is scanned by emergency response personnel to verify identity of subscriber using the biometric identifier of the subscriber.

3. The method of claim 1 wherein the biometric identifier is a string of a plurality of characters.

4. The method of claim 3 further comprising generating the biometric identifier, wherein the step of generating the biometric identifier comprises adding a client code to the string to generate an aggregate code and then hashing the aggregate code to generate the biometric identifier.

5. The method of claim 4 wherein the aggregate code further comprises a unique user identifier (UUID), the UUID added to the client code and the string.

6. The method of claim 1 further comprising the step of accessing a central prescription database; identifying active prescriptions; and including the active prescription in the medical information.

7. The method of claim 1 wherein the first software application is stored in a SIM card of the first mobile device.

8. The method of claim 7 wherein the first software application controls one or more network protocols installed on the first mobile device, wherein the network protocols support direct communication between the first mobile device and a second mobile device during a telecommunication network service provider outage.

9. The method of claim 1 further comprising generating one or more alerts based upon frequency of the subscriber's prescriptions being written or category of prescriptions, wherein the category is selected from the group consisting of pain medication, antidepressants, stimulants, and schedule II medications.

10. The method of claim 1 wherein the medical information is selected from the group consisting of allergies, active medications, prior medications, vital or acute medical history, name, age, gender, blood type and date of birth.

11. The method of claim 1 further comprising downloading, prior to the occurrence of the network outage, a secure file containing one or more profiles of subscribers to a local device on a predetermined schedule to generate a local truncated set of medical records based on subscriber location.

12. The method of claim 1 further comprising the step of accessing a third party source of data; retrieving updated information from the third party source of data and updating the medical information using the updated information.

13. The method of claim 1 further comprising detecting the network outage, accessing the first software application upon occurrence of a network outage, wherein detecting the network outage renders the first software application accessible.

14. The system of claim 13, wherein the interconnected network of mobile devices is interconnected using an Unstructured Supplementary Services Data (USSD) protocol and a USSD gateway.

15. A computer system for securely retrieving remotely stored data for an individual having a medical emergency, the computer system comprising:

an electronic memory device; and an electronic processor in communication with the memory device, wherein the memory device comprises instructions that when executed by the processor cause the processor to:

store a first software application in a persistent electronic memory device of a plurality of mobile devices, initiate, in response to detecting a network outage, communication with the plurality of mobile devices to establish an interconnected network of mobile devices to exchange medical information for an enrolled subscriber using the first software application;

store medical information for the enrolled subscriber to emergency response service in a data storage device at one or more remote locations or on one or more mobile devices of the plurality of mobile devices;

store a biometric identifier for the subscriber to emergency response service at one or more locations or on one or more mobile devices of the plurality of mobile devices;

correlate the biometric identifier and medical information on a per subscriber basis; and transmit or access the medical information in response to receiving an aggregate identifier generated in response to a scan of the enrolled subscriber using a mobile device of the plurality of mobile devices.

16. The system of claim 15 further comprising instructions to cause the processor to access a third party source of data; retrieve updated information from the third party source of data and update the medical information using the updated information.

17. The system of claim 15 further comprising instructions to cause the processor to generate the biometric identifier, wherein the step of generating the biometric identifier comprises adding a client code to a template to generate an aggregate code and then hashing the aggregate code to generate the biometric identifier.

18. The system of claim 15 further comprising instructions to cause the processor to run one or more application servers, the one or more application servers running an emergency data retrieval software application.

19. The system of claim 15 further comprising a first database to store session information comprising one or more aggregate identifiers.

20. The system of claim 15 further comprising a second database to store one or more subscriber records, the subscriber records comprising a set of sensitive medical information.

* * * * *